United States Patent
Cloninger

(10) Patent No.: US 11,200,972 B2
(45) Date of Patent: Dec. 14, 2021

(54) SYSTEM, APPARATUS, AND METHOD FOR DISPENSARY MANAGEMENT

(71) Applicant: Timothy N. Cloninger, Hoffman Estates, IL (US)

(72) Inventor: Timothy N. Cloninger, Hoffman Estates, IL (US)

(73) Assignee: Accu-Chart Plus Healthcare Systems, Inc., Schaumburg, IL (US)

( * ) Notice: Subject to any disclaimer, the term of this patent is extended or adjusted under 35 U.S.C. 154(b) by 812 days.

(21) Appl. No.: 15/659,571

(22) Filed: Jul. 25, 2017

(65) Prior Publication Data

US 2018/0151257 A1 May 31, 2018

Related U.S. Application Data

(60) Provisional application No. 62/366,392, filed on Jul. 25, 2016.

(51) Int. Cl.
*G16H 20/13* (2018.01)
*A61J 7/00* (2006.01)
(Continued)

(52) U.S. Cl.
CPC ............ *G16H 20/13* (2018.01); *A61J 7/0076* (2013.01); *B65B 69/0033* (2013.01);
(Continued)

(58) Field of Classification Search
CPC ........ G16H 20/13; G16H 40/20; G16H 30/20; A61J 7/0076; A61J 1/035; A61J 2205/10;
(Continued)

(56) References Cited

U.S. PATENT DOCUMENTS

2006/0071011 A1* 4/2006 Varvarelis ........... G07F 17/0092
221/9
2007/0208454 A1* 9/2007 Forrester ................. G07F 11/00
700/216
(Continued)

*Primary Examiner* — Fonya M Long
*Assistant Examiner* — Anthony Michael Balaj
(74) *Attorney, Agent, or Firm* — Christopher J. Scott

(57) ABSTRACT

A computerized dispensary management system and method enhances dispensary product management and are supported by a blister pack separation apparatus. The system and method operate according to a computer-implementable application and at least one computer. A scanner system further cooperates with the application and computer for scan-inputting product- and person-identifying machine-readable code information to the application for processing. The person-identifying code is scannable to identify a person and a product regimen for the person. The application provides a series of sequential screenshots based upon basic filler and dispenser screenshots for filler and dispenser side product management, guiding the user through a regimen-filling and administration. The processes are characterized by screenshot re-arrangements occurring thereto as each successive code is scanned. The blister pack separation apparatus operates to simultaneously sever individual blister pack units therefrom, which units are then outfitted with machine-readable code and thus made scannable by the system.

10 Claims, 44 Drawing Sheets

Figure 10:
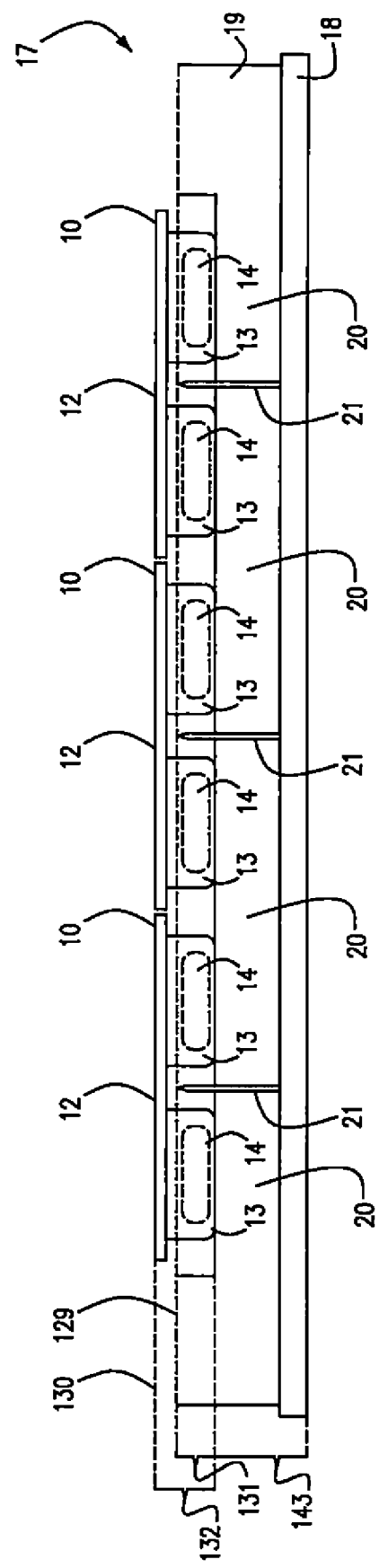
Figure 14:
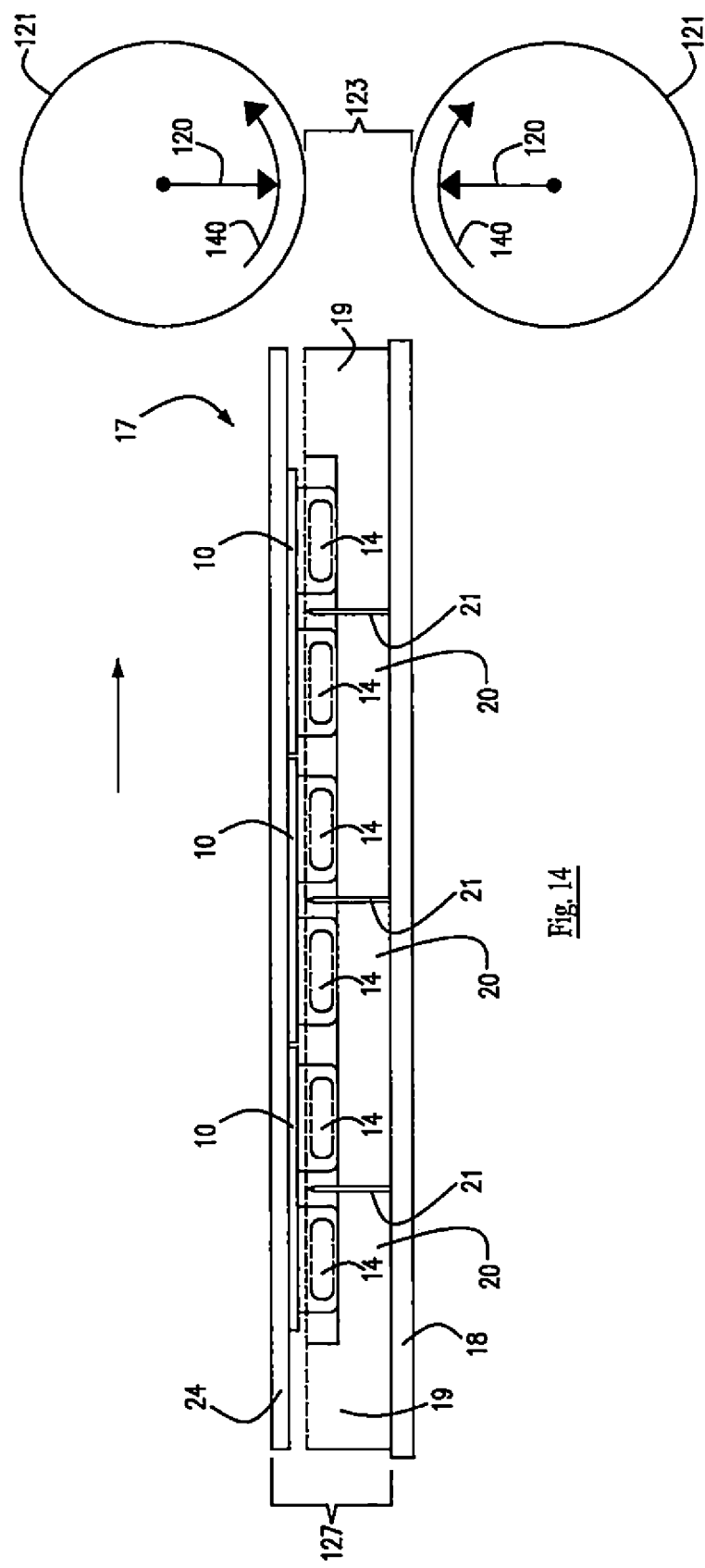
Figure 15:
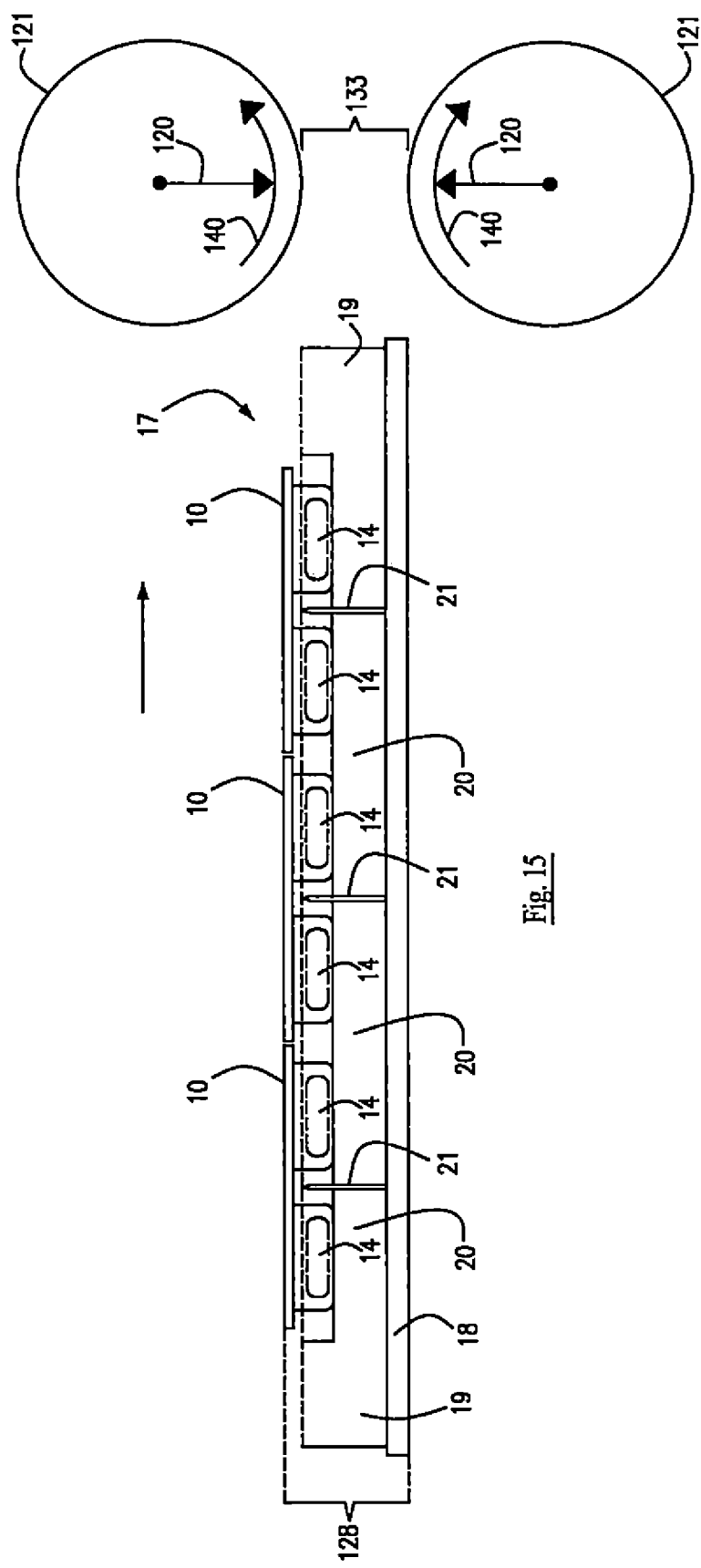
Figure 16:
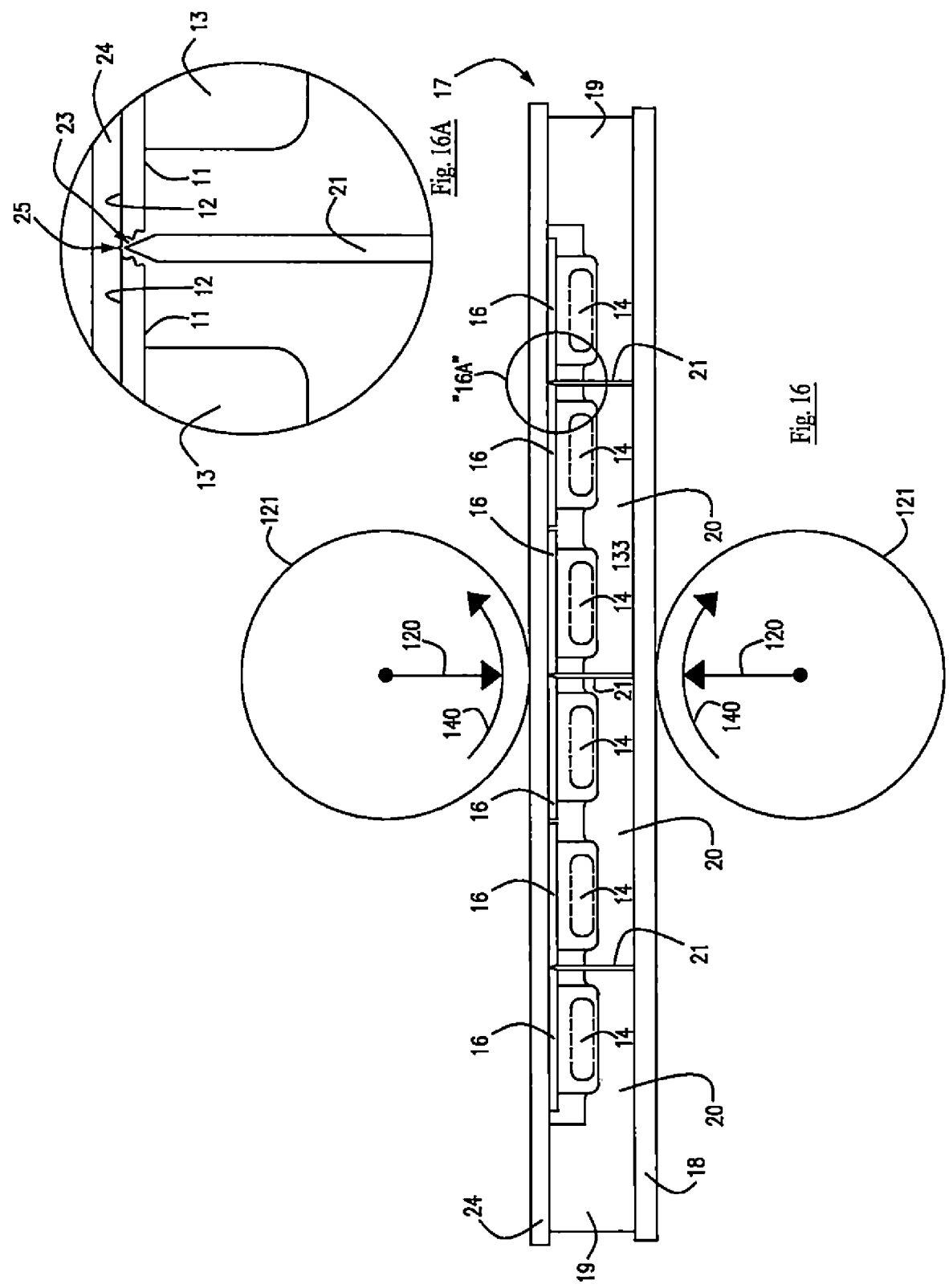
Figure 17:
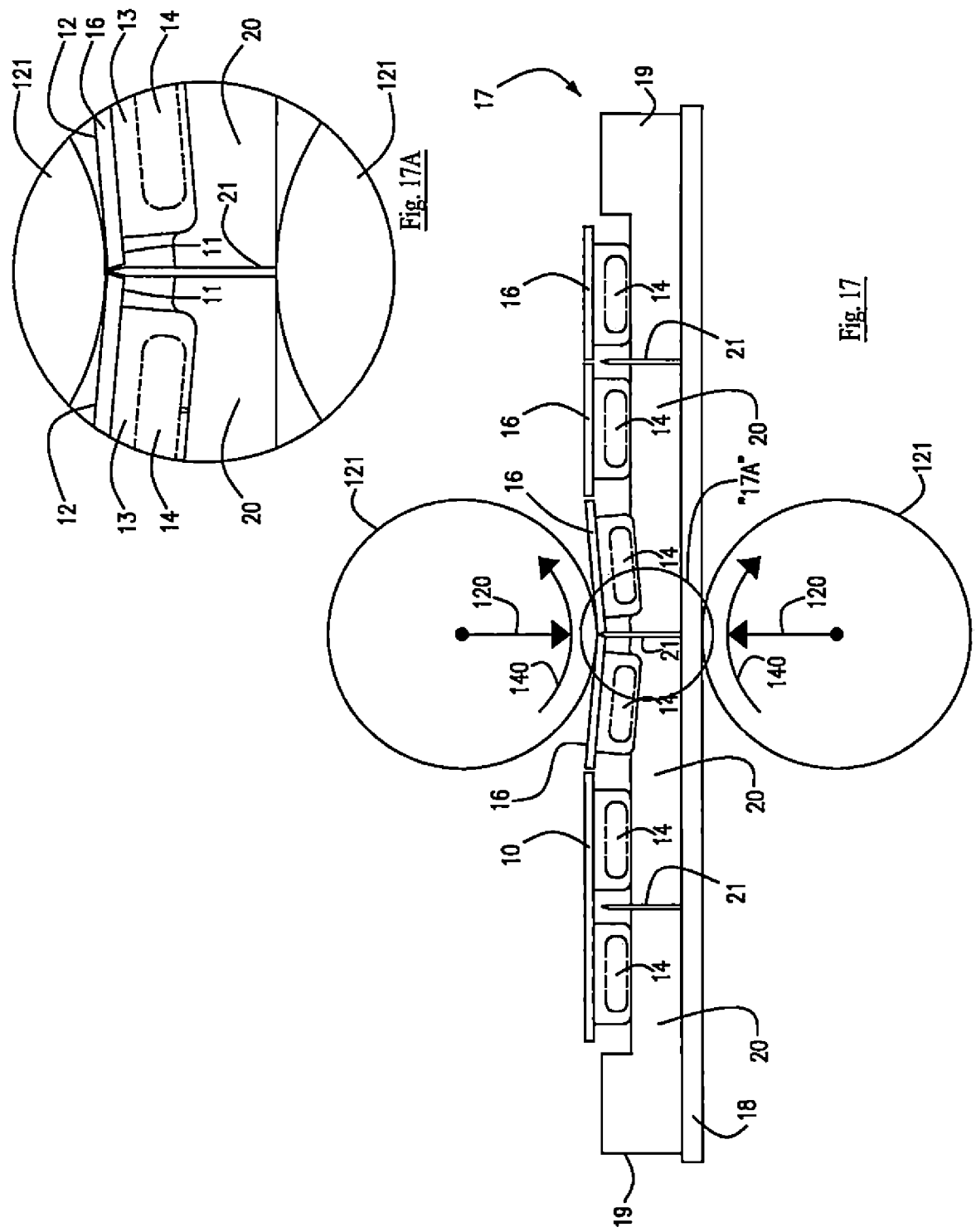
Figures 18, 19:
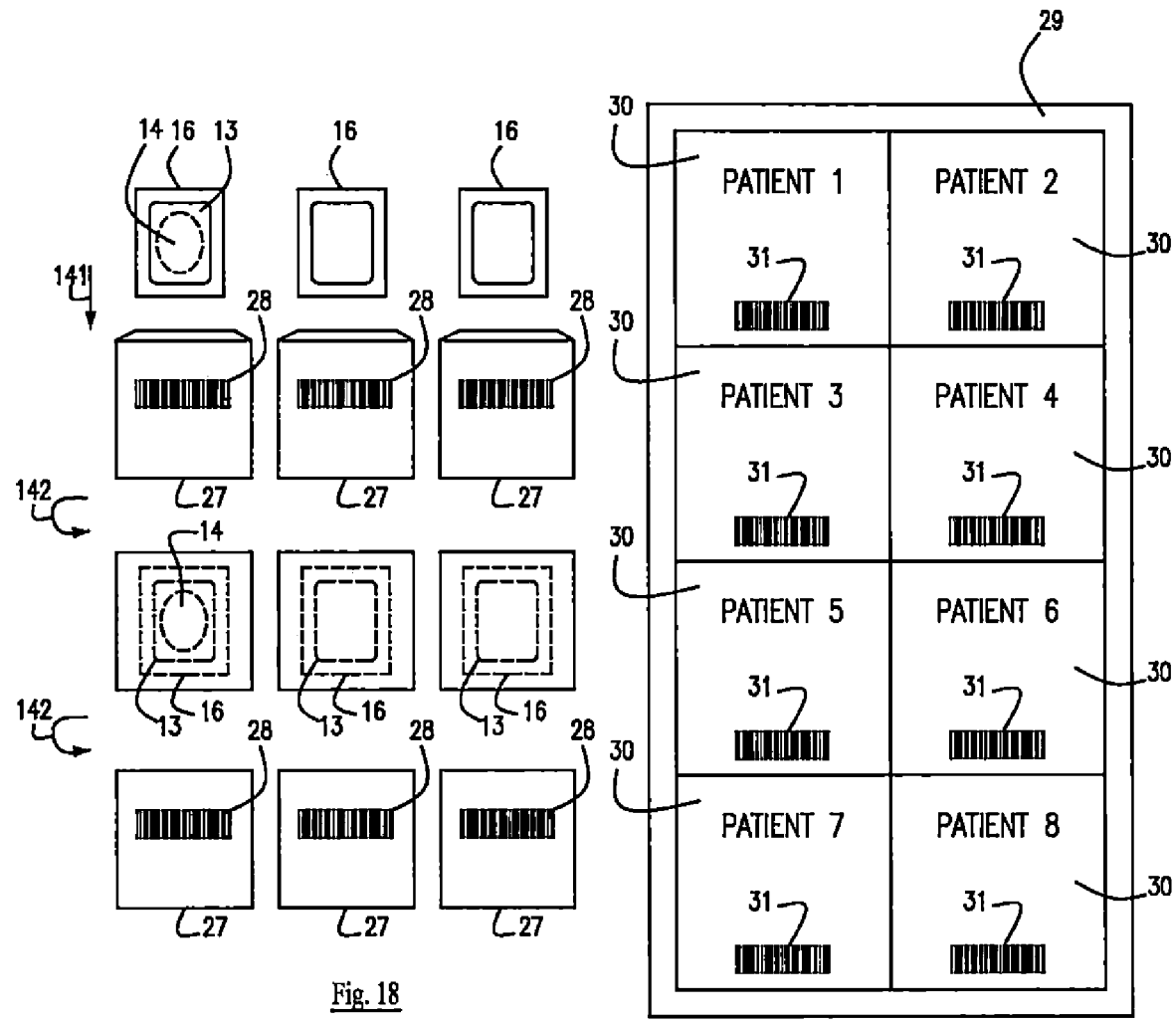
Figure 20:
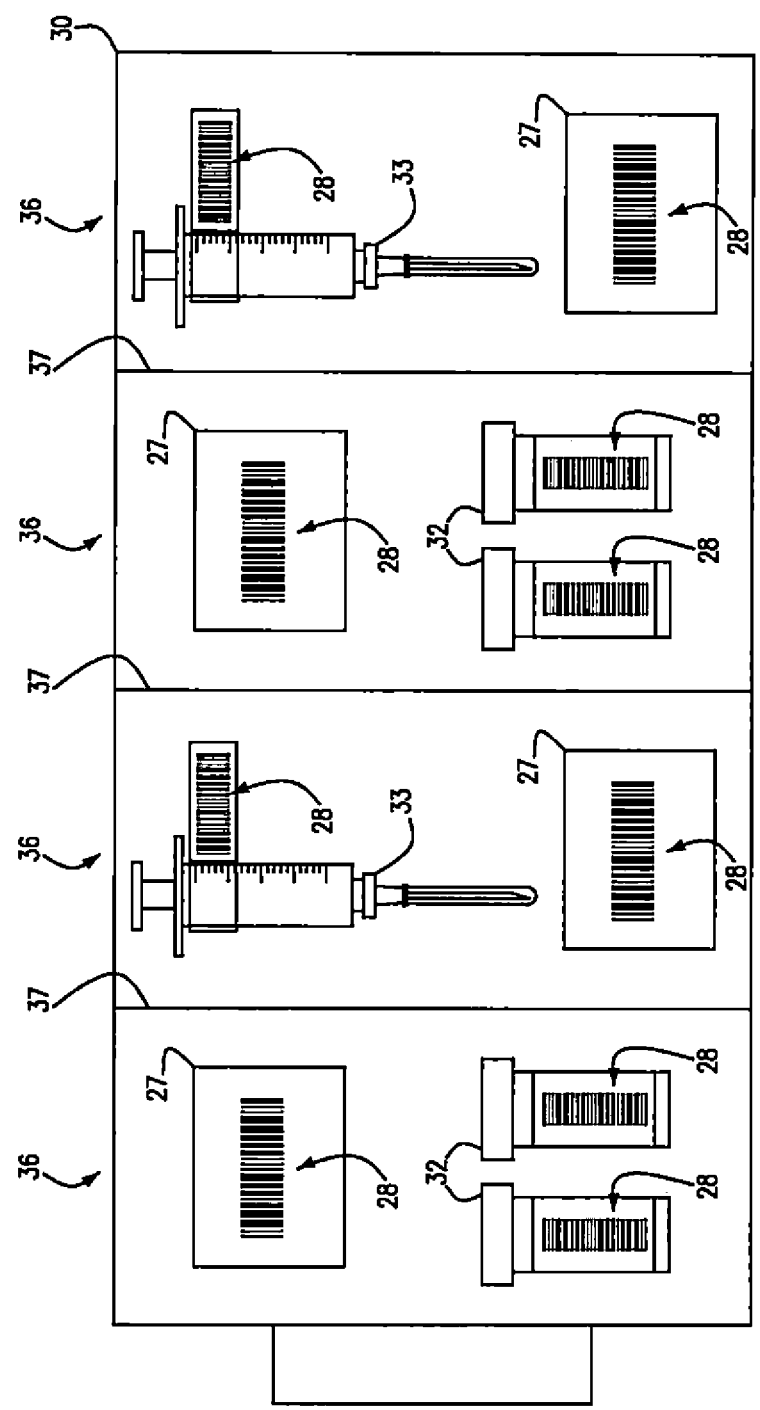
Figure 28:
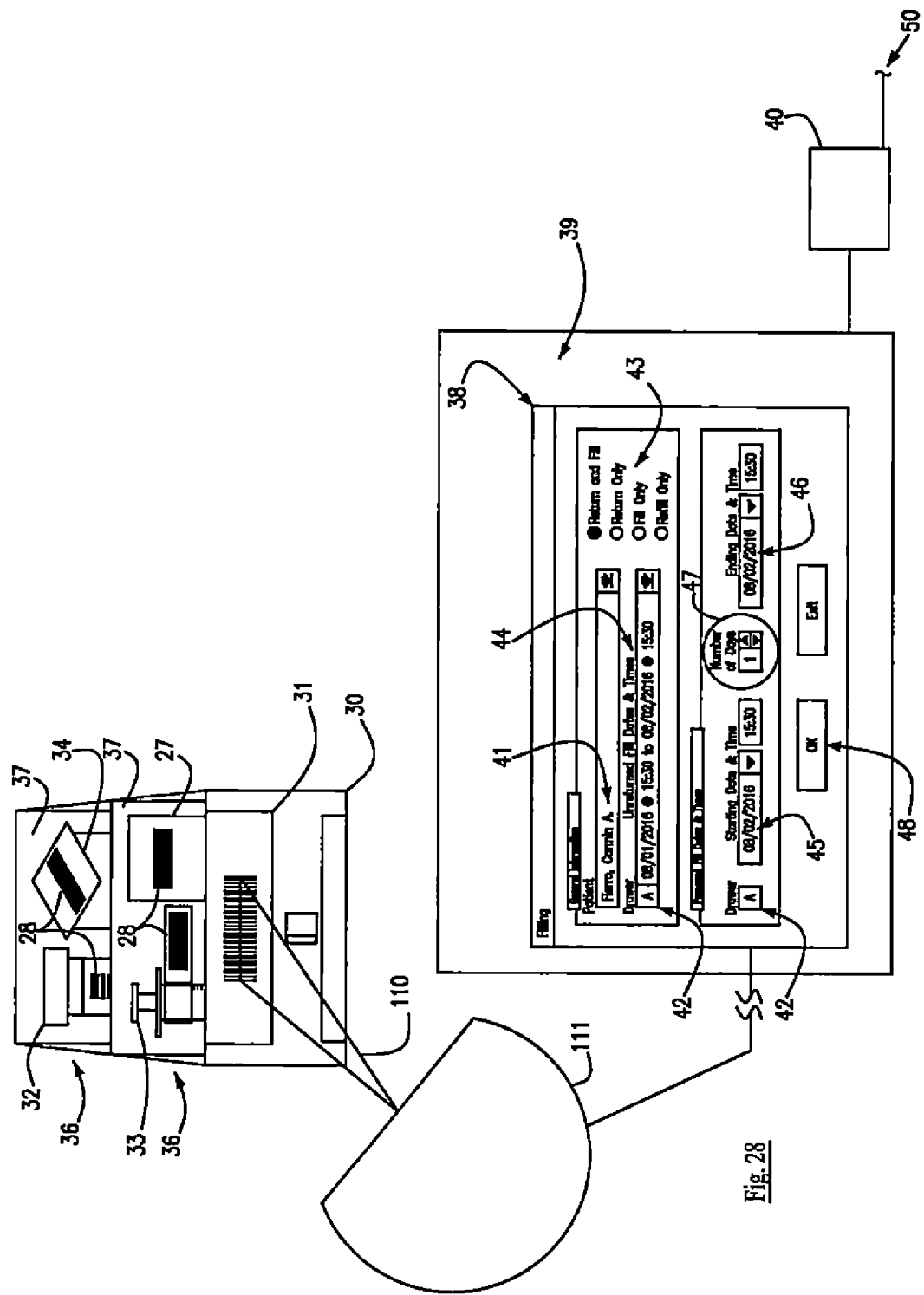
Figure 34:
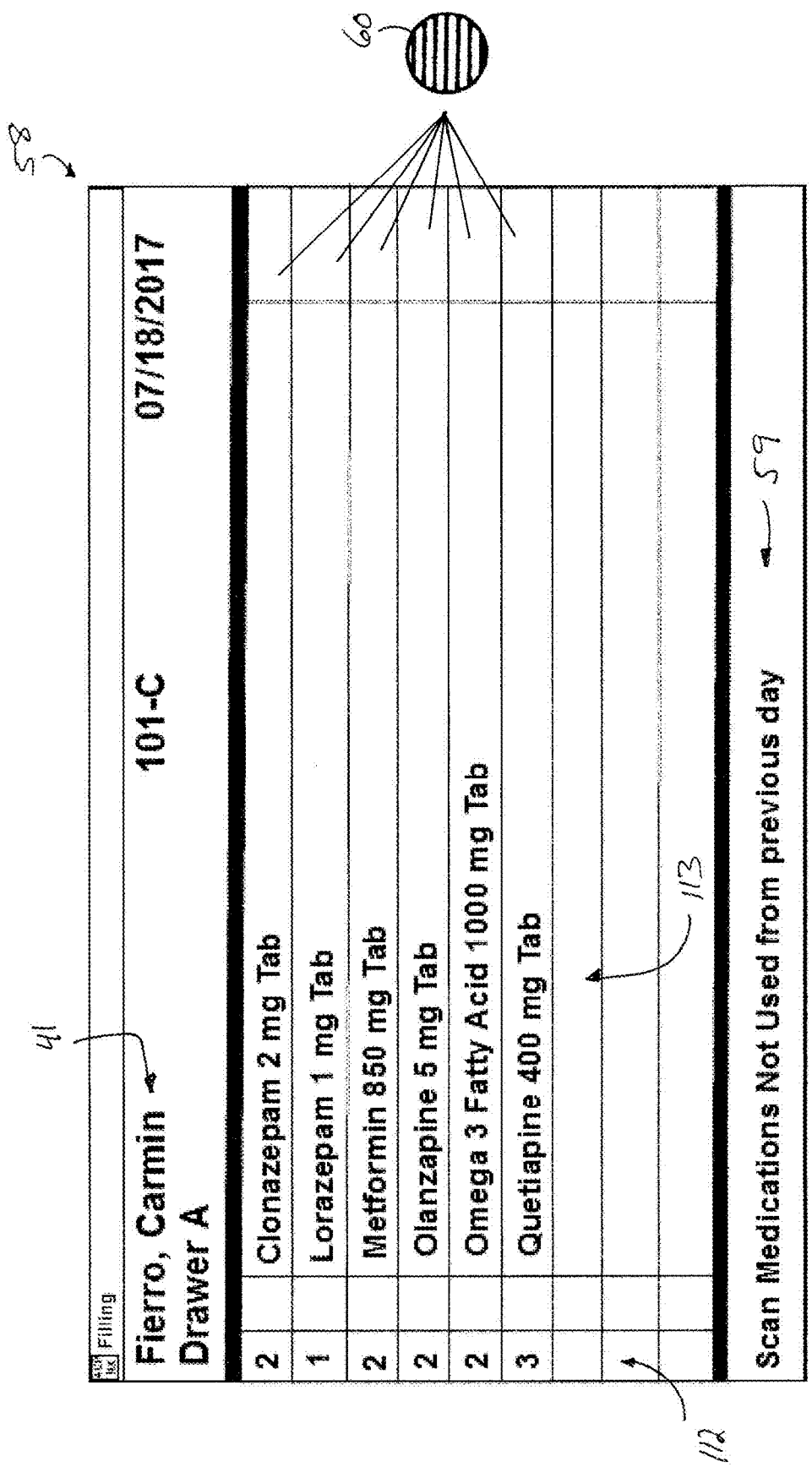
Figure 35:
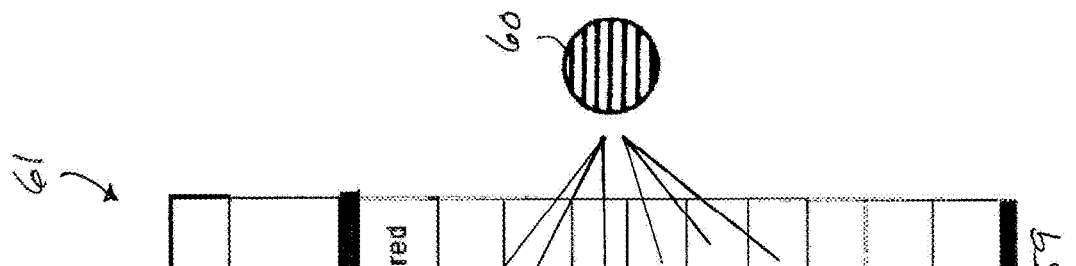
Figure 45:
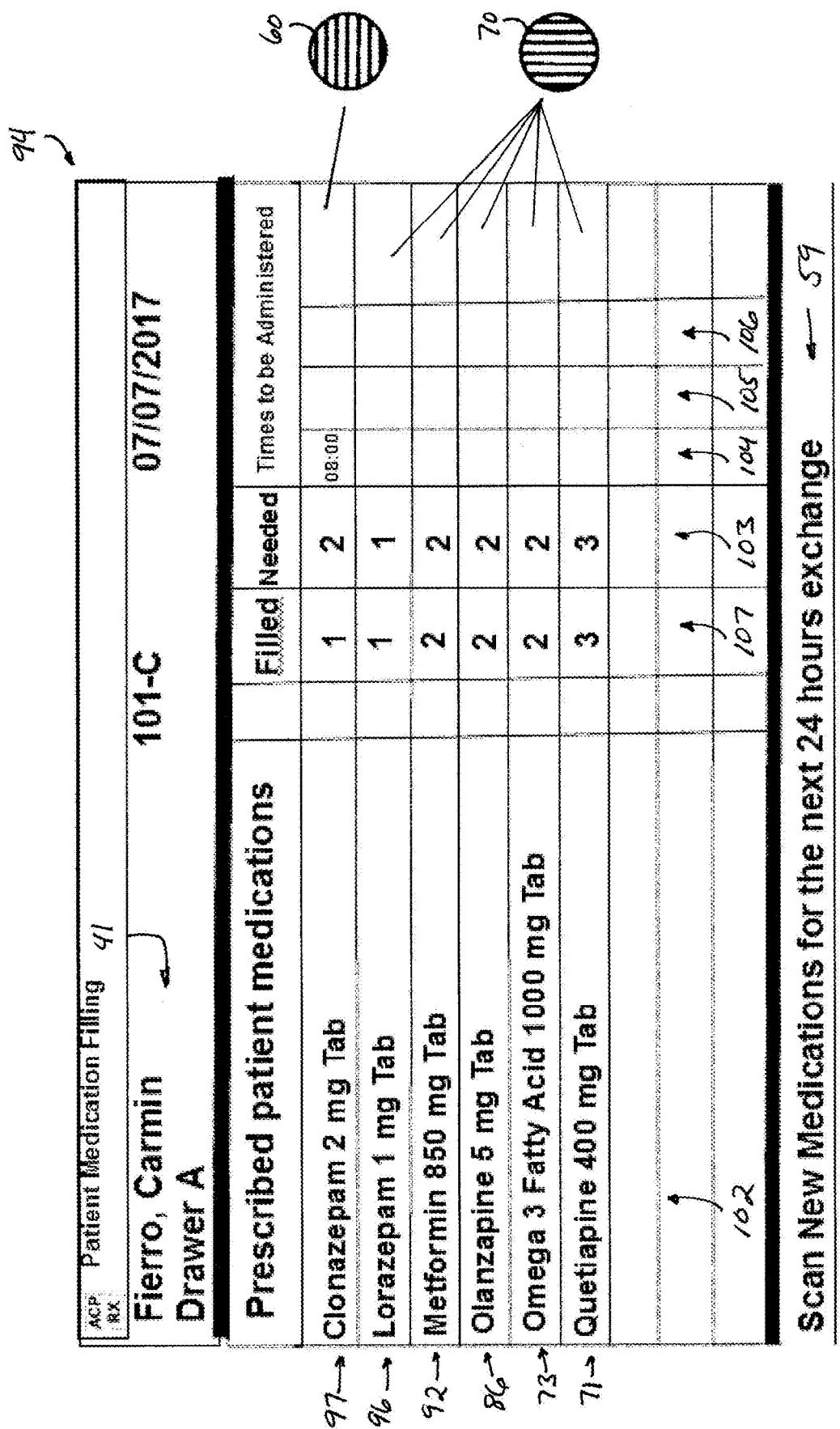
Figure 55:

(51) Int. Cl.
  *B65B 69/00* (2006.01)
  *G16H 30/20* (2018.01)
  *G16H 40/20* (2018.01)
  *A61J 1/03* (2006.01)

(52) U.S. Cl.
  CPC .............. *G16H 30/20* (2018.01); *G16H 40/20* (2018.01); *A61J 1/035* (2013.01); *A61J 2205/10* (2013.01); *A61J 2205/20* (2013.01); *A61J 2205/70* (2013.01)

(58) Field of Classification Search
  CPC .............. A61J 2205/20; A61J 2205/70; B65B 69/0033
  See application file for complete search history.

(56) References Cited

U.S. PATENT DOCUMENTS

| | | | |
|---|---|---|---|
| 2009/0287350 A1* | 11/2009 | Johnson | G07F 17/0092 700/236 |
| 2016/0143807 A1* | 5/2016 | Ika | A61J 1/03 206/216 |
| 2016/0147976 A1* | 5/2016 | Jain | A61J 7/0084 705/2 |

* cited by examiner

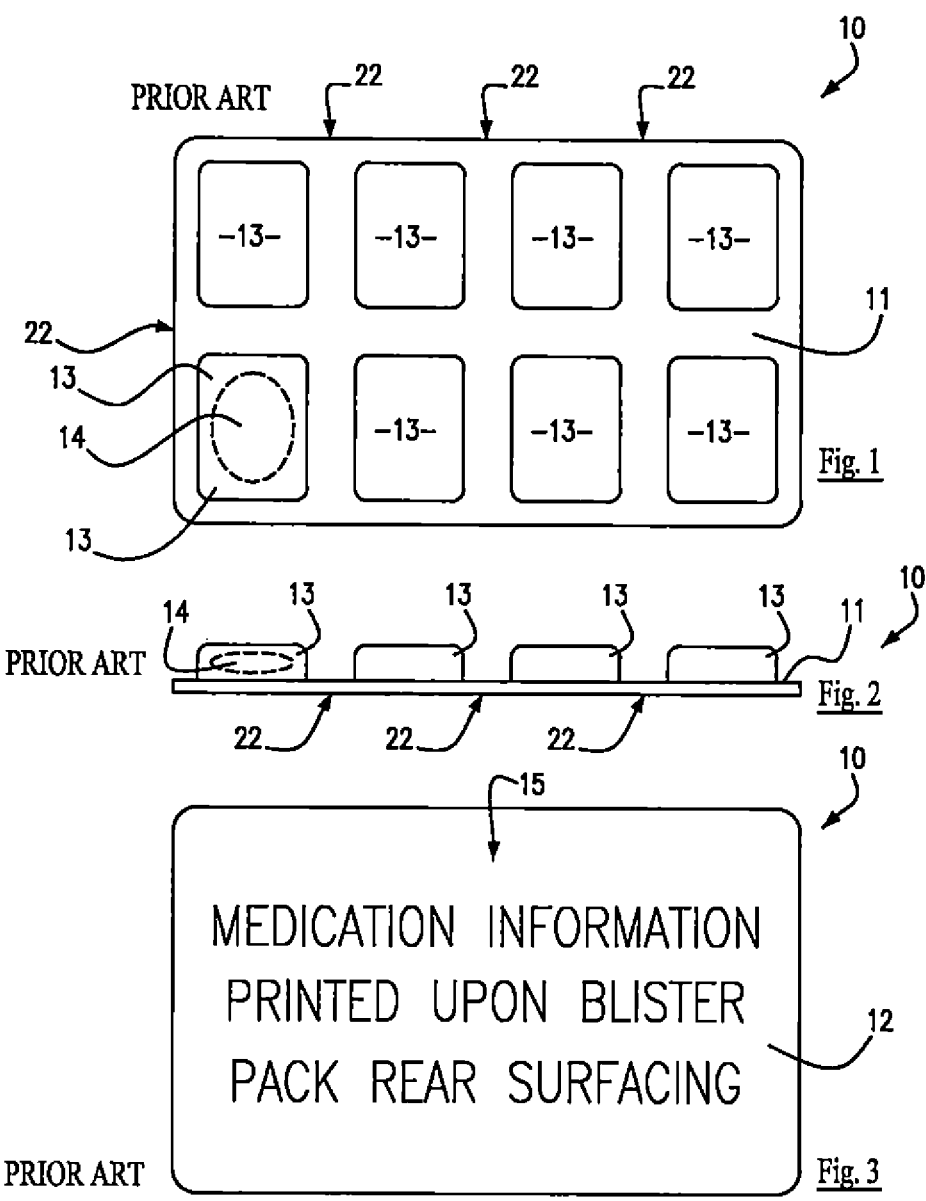

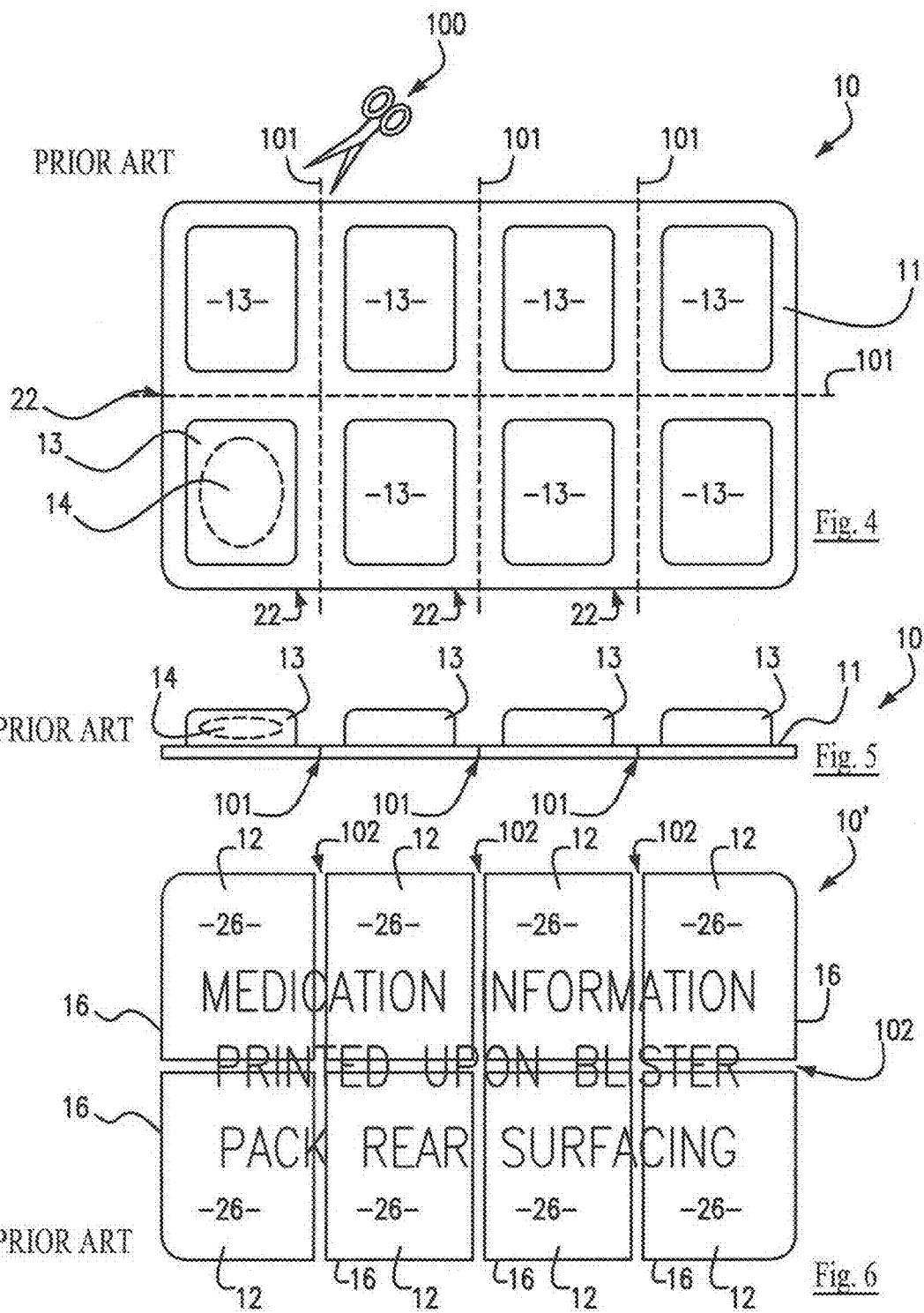

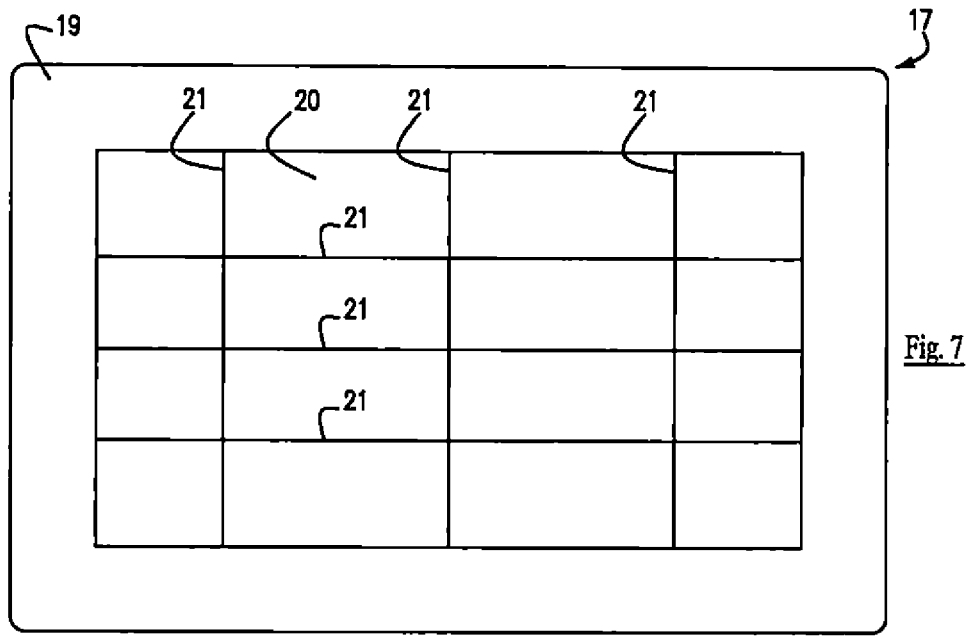
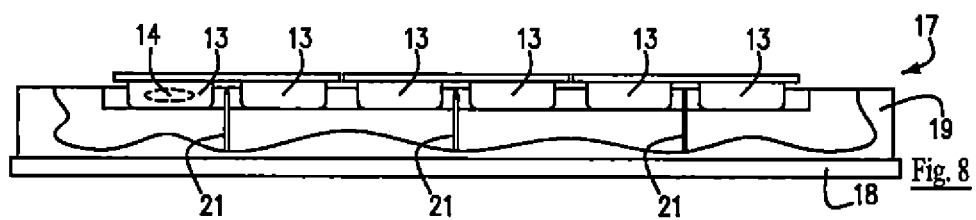
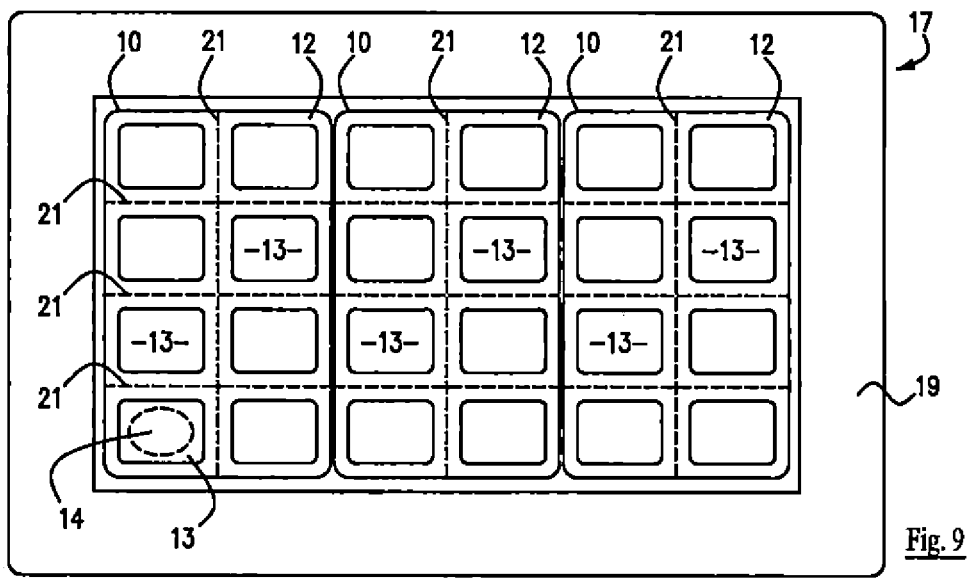

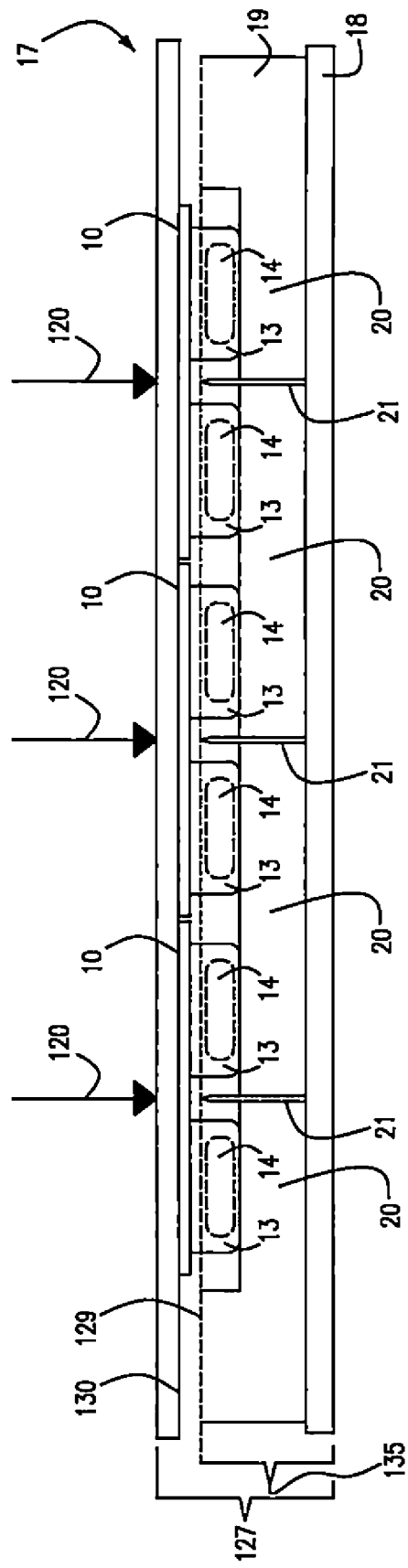

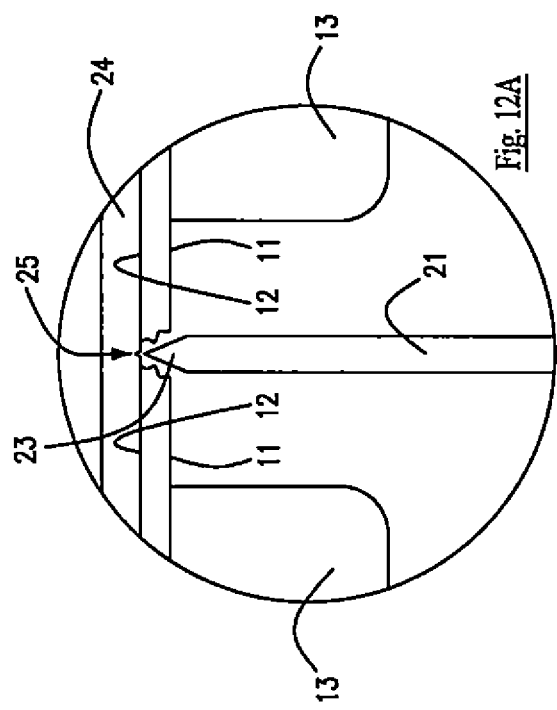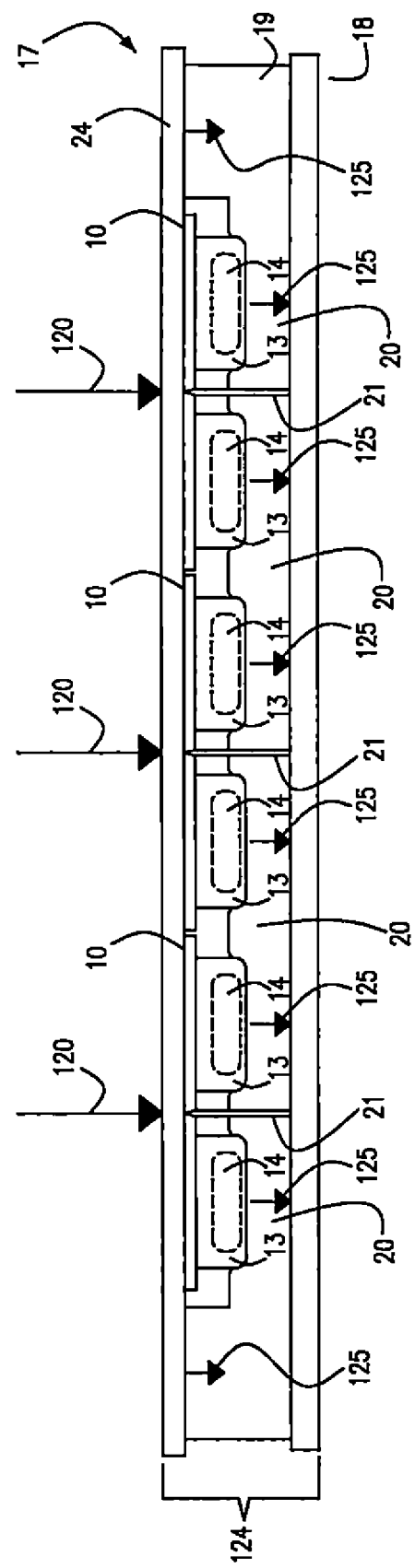

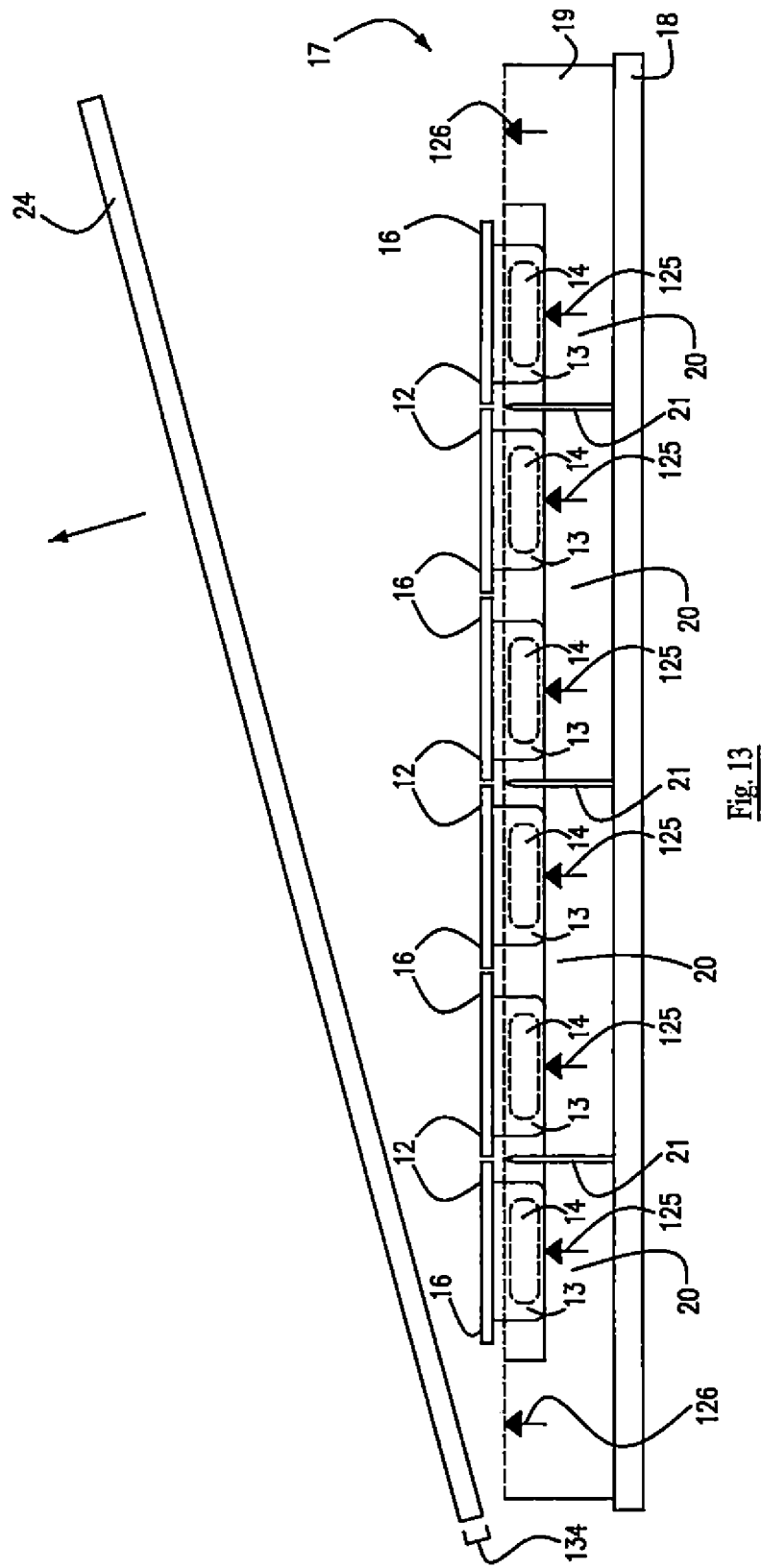

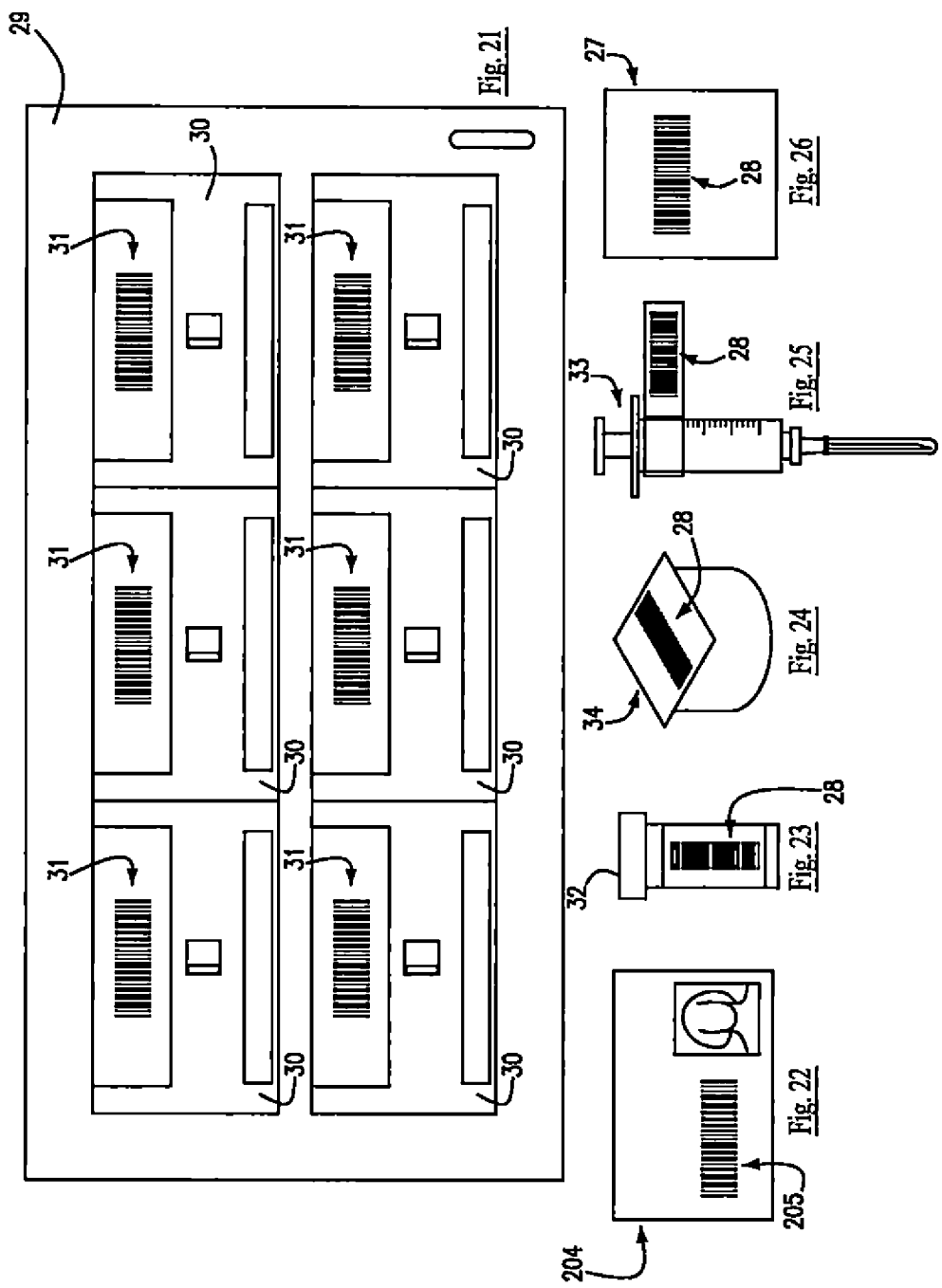

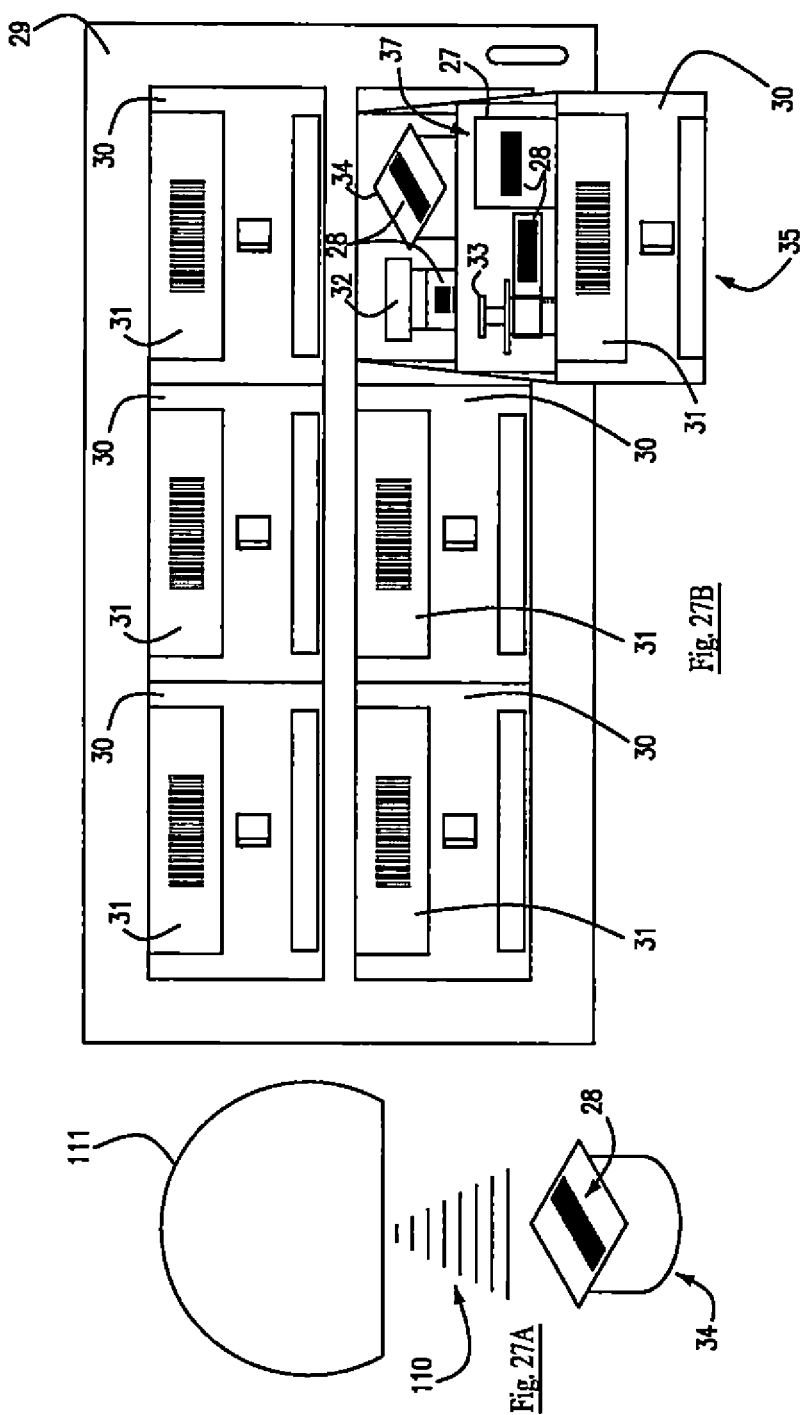

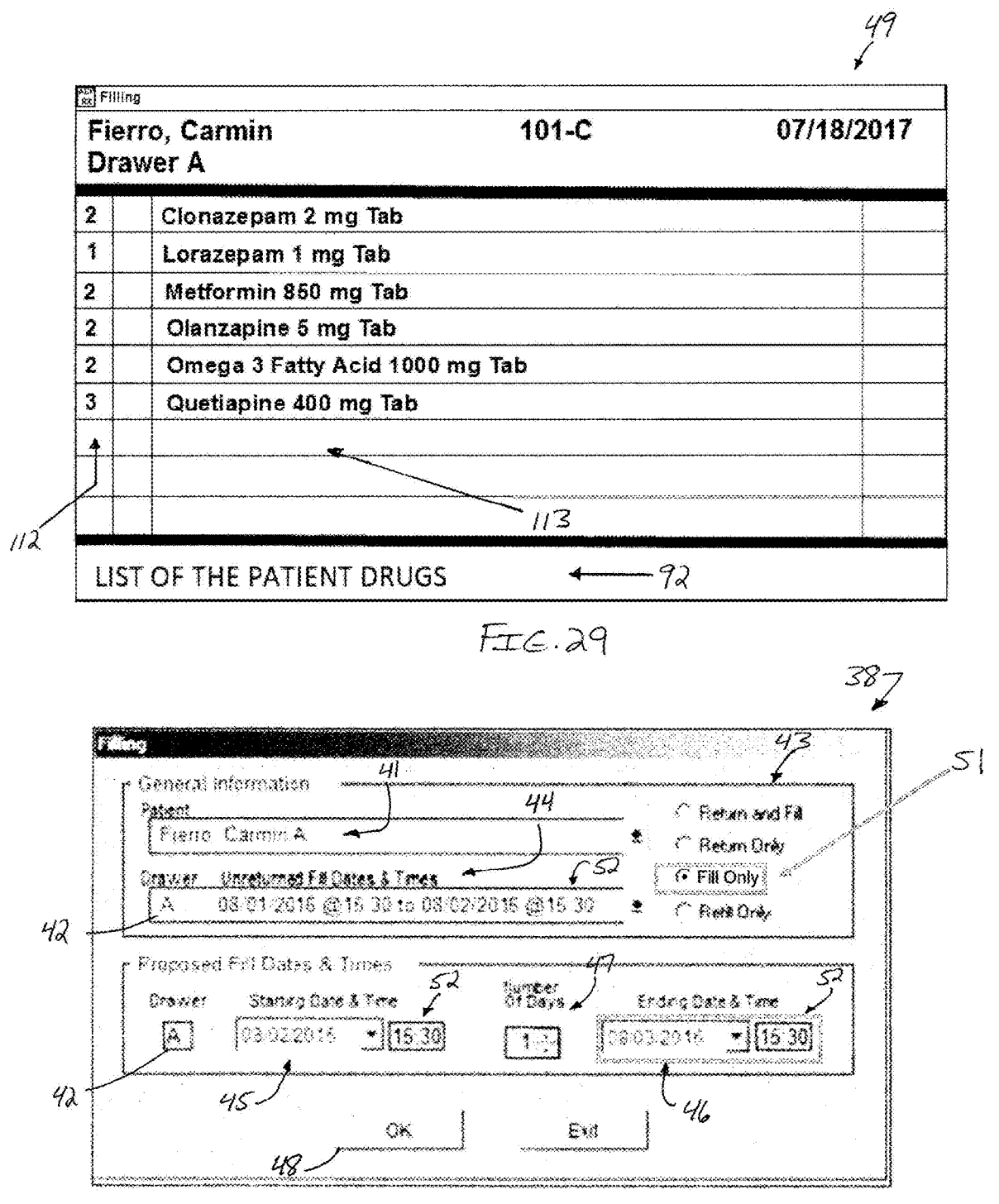

| Filling | | | |
|---|---|---|---|
| Fierro, Carmin  Drawer A | | 101-C | 07/18/2017 |
| 2 | Clonazepam 2 mg Tab | | |
| 1 | Lorazepam 1 mg Tab | | |
| 2 | Metformin 850 mg Tab | | |
| 2 | Olanzapine 5 mg Tab | | |
| 2 | Omega 3 Fatty Acid 1000 mg Tab | | |
| 3 | Quetiapine 400 mg Tab | | |
| | | | |
| LIST OF THE PATIENT DRUGS | | | |

FIG. 29

FIG. 30

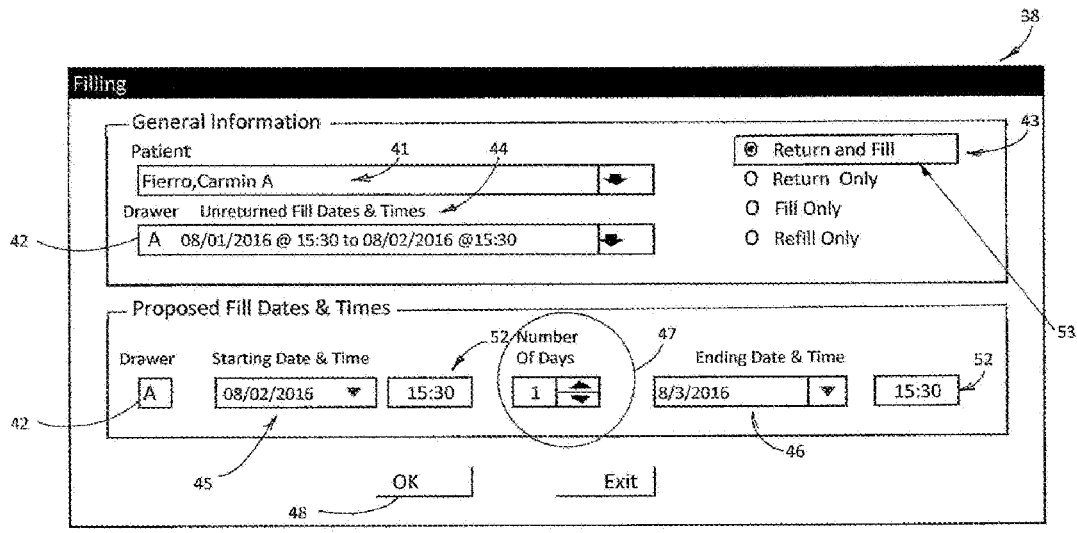
FIG.31
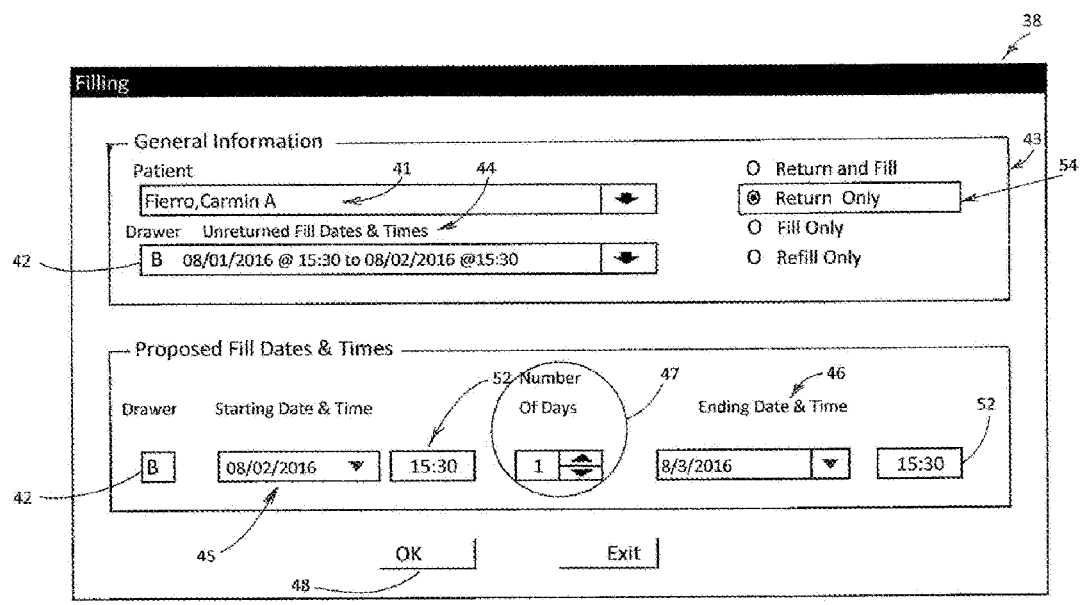
FIG.32
| Patient Name | Patient Number | Monday Letter | Tuesday Letter | Wednesday Letter | Thursday Letter | Friday Letter |
|---|---|---|---|---|---|---|
| Carmin Fierro | 1004034 | A | B | A | B | A |
| | Patient Scan Code | ~9A1004034 | ~9B1004034 | ~9A1004034 | ~9B1004034 | ~9A1004034 |
FIG.33

| ACP RX | Patient Medication Filling 41 | | | |
|---|---|---|---|---|
| Fierro, Carmin<br>Drawer A | | 101-C | | 07/07/2017 |
| Prescribed patient medications | | Filled | Needed | Times to be Administered |
| Clonazepam 2 mg Tab | | 0 | 2 | 20:00  08:00 |
| Lorazepam 1 mg Tab | | 0 | 1 | 08:00 |
| Metformin 850 mg Tab | | 0 | 2 | 20:00  08:00 |
| Olanzapine 5 mg Tab | | 0 | 2 | 20:00  08:00 |
| Omega 3 Fatty Acid 1000 mg Tab | | 0 | 2 | 20:00  08:00 |
| Quetiapine 400 mg Tab | | 1 | 3 | 08:00  14:00 |

Scan New Medications for the next 24 hours exchange — 59

FIG. 36

| ACP Patient Medication Filling 41 | | | |
|---|---|---|---|
| Fierro, Carmin<br>Drawer A | 101-C | | 07/07/2017 |

| Prescribed patient medications | Filled | Needed | Times to be Administered |
|---|---|---|---|
| Clonazepam 2 mg Tab | 0 | 2 | 20:00  08:00 |
| Lorazepam 1 mg Tab | 0 | 1 | 08:00 |
| Metformin 850 mg Tab | 0 | 2 | 20:00  08:00 |
| Olanzapine 5 mg Tab | 0 | 2 | 20:00  08:00 |
| Omega 3 Fatty Acid 1000 mg Tab | 2 | 2 | 20:00  08:00 |
| Quetiapine 400 mg Tab | | 3 | 20:00  14:00  08:00 |

Scan New Medications for the next 24 hours exchange

FIG. 37

Patient Medication Filling 41

| Fierro, Carmin Drawer A | 101-C | | 07/07/2017 | |
|---|---|---|---|---|
| Prescribed patient medications | Filled | Needed | Times to be Administered | |
| Clonazepam 2 mg Tab | 0 | 2 | 20:00 | 08:00 |
| Lorazepam 1 mg Tab | 0 | 1 | | 08:00 |
| Metformin 850 mg Tab | 0 | 2 | 20:00 | 08:00 |
| Olanzapine 5 mg Tab | 0 | 2 | 20:00 | 08:00 |
| Quetiapine 400 mg Tab | 3 | 3 | 20:00 | 08:00 |

Scan New Medications for the next 24 hours exchange

FIG. 38

| ACP Patient Medication Filling 41 | | | |
|---|---|---|---|
| Fierro, Carmin<br>Drawer A | 101-C | | 07/07/2017 |
| Prescribed patient medications | Filled | Needed | Times to be Administered |
| Clonazepam 2 mg Tab | 0 | 2 | 20:00 08:00 |
| Lorazepam 1 mg Tab | 0 | 1 | 08:00 |
| Metformin 850 mg Tab | 0 | 2 | 20:00 08:00 |
| Olanzapine 5 mg Tab | 1 | 2 | 08:00 |
| Omega 3 Fatty Acid 1000 mg Tab | | 2 | |
| Quetiapine 400 mg Tab | 3 | 3 | |

Scan New Medications for the next 24 hours exchange

FIG. 39

| ACP RX | Patient Medication Filling 41 | | | | |
|---|---|---|---|---|---|
| Fierro, Carmin<br>Drawer A | | 101-C | | | 07/07/2017 |
| Prescribed patient medications | Filled | Needed | | Times to be Administered | |
| Clonazepam 2 mg Tab | 0 | 2 | | 20:00 | 08:00 |
| Lorazepam 1 mg Tab | 0 | 1 | 84 | | 08:00 |
| Metformin 850 mg Tab | 0 | 2 | | 20:00 | 08:00 |
| Olanzapine 5 mg Tab | 2 | 2 | | 20:00 | 08:00 |
| Omega 3 Fatty Acid 1000 mg Tab | 3 | 3 | | | |
| Quetiapine 400 mg Tab | | | | | |

Scan New Medications for the next 24 hours exchange

FIG. 40

FIG. 41

| AGP Patient Medication Filling 41 | | | | |
|---|---|---|---|---|
| Fierro, Carmin | 101-C | | | 07/07/2017 |
| Drawer A | | | | |
| Prescribed patient medications | Filled | Needed | Times to be Administered | |
| Clonazepam 2 mg Tab | 0 | 2 | 20:00 | 08:00 — 88 |
| Lorazepam 1 mg Tab — 89 | 0 | 1 | 08:00 — 84 | |
| Metformin 850 mg Tab | 2 — 82 | 2 — 83 | 20:00 | 08:00 — 85 |
| Olanzapine 5 mg Tab — 86 | 2 | 2 | | |
| Omega 3 Fatty Acid 1000 mg Tab — 73 | 3 | 3 | | |
| Quetiapine 400 mg Tab — 71 | ← 107 | ← 103 | ← 104 | ← 105 106 |
| Scan New Medications for the next 24 hours exchange ← 59 | | | | |

↑ 102

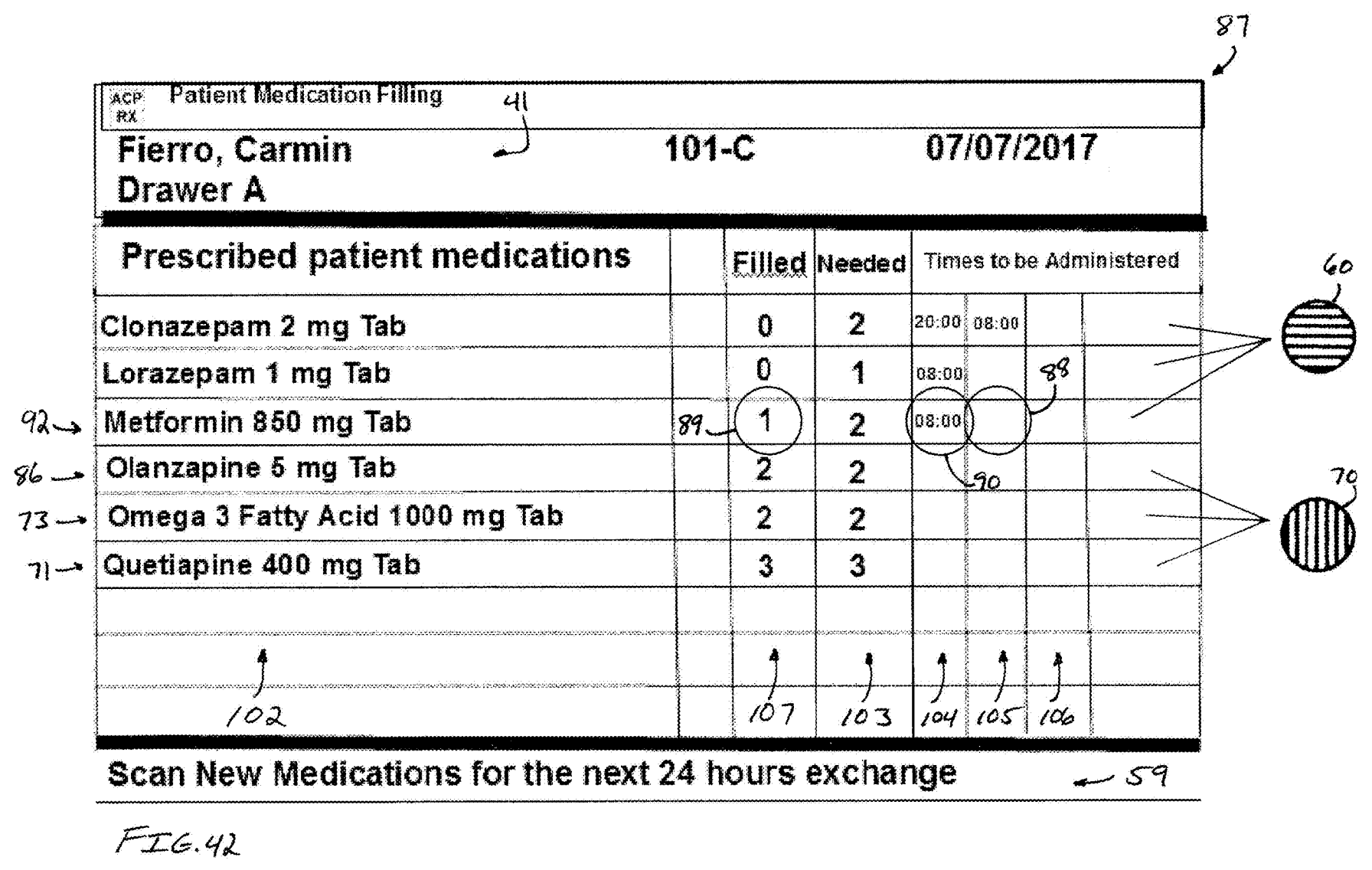

| ACP Patient Medication Filling 41 | | | | |
|---|---|---|---|---|
| Fierro, Carmin    101-C    07/07/2017 Drawer A | | | | |
| Prescribed patient medications | Filled | Needed | Times to be Administered | |
| Clonazepam 2 mg Tab | 0 | 2 | | 20:00 |
| Lorazepam 1 mg Tab | 0 | 1 | | |
| Metformin 850 mg Tab | 1 | 2 | 08:00 | 08:00 |
| Olanzapine 5 mg Tab | 2 | 2 | | |
| Omega 3 Fatty Acid 1000 mg Tab | 2 | 2 | | |
| Quetiapine 400 mg Tab | 3 | 3 | | |

Scan New Medications for the next 24 hours exchange

FIG. 42

FIG. 43

| Patient Medication Filling 41 | | | | |
|---|---|---|---|---|
| Fierro, Carmin 101-C 07/07/2017 Drawer A | | | | |
| Prescribed patient medications | Filled | Needed | Times to be Administered | |
| Clonazepam 2 mg Tab | 0 | 2 | 20:00 | 08:00 |
| Lorazepam 1 mg Tab | 0 | 1 | 08:00 | |
| Metformin 850 mg Tab | 2 | 2 | | |
| Olanzapine 5 mg Tab | 2 | 2 | | |
| Omega 3 Fatty Acid 1000 mg Tab | 2 | 2 | | |
| Quetiapine 400 mg Tab | 3 | 3 | | |

Scan New Medications for the next 24 hours exchange

| ACP RX | Patient Medication Filling 41 | | | | |
|---|---|---|---|---|---|
| Fierro, Carmin | | 101-C | | 07/07/2017 | |
| Drawer A | | | | | |
| Prescribed patient medications | | Filled | Needed | Times to be Administered | |
| | | | | 20:00 | 08:00 |
| 97→ Clonazepam 2 mg Tab | | 0 | 2 | | |
| 96→ Lorazepam 1 mg Tab | | 1 | 1 | | |
| 92→ Metformin 850 mg Tab | | 2 | 2 | | |
| 86→ Olanzapine 5 mg Tab | | 2 | 2 | | |
| 73→ Omega 3 Fatty Acid 1000 mg Tab | | 2 | 2 | | |
| 71→ Quetiapine 400 mg Tab | | 3 | 3 | | |
| | | ↑ 107 | ↑ 103 | ↑ 104 | 105 ↑ 106 |
| ↑ 102 | | | | | |
| Scan New Medications for the next 24 hours exchange ← 59 | | | | | |

FIG. 44

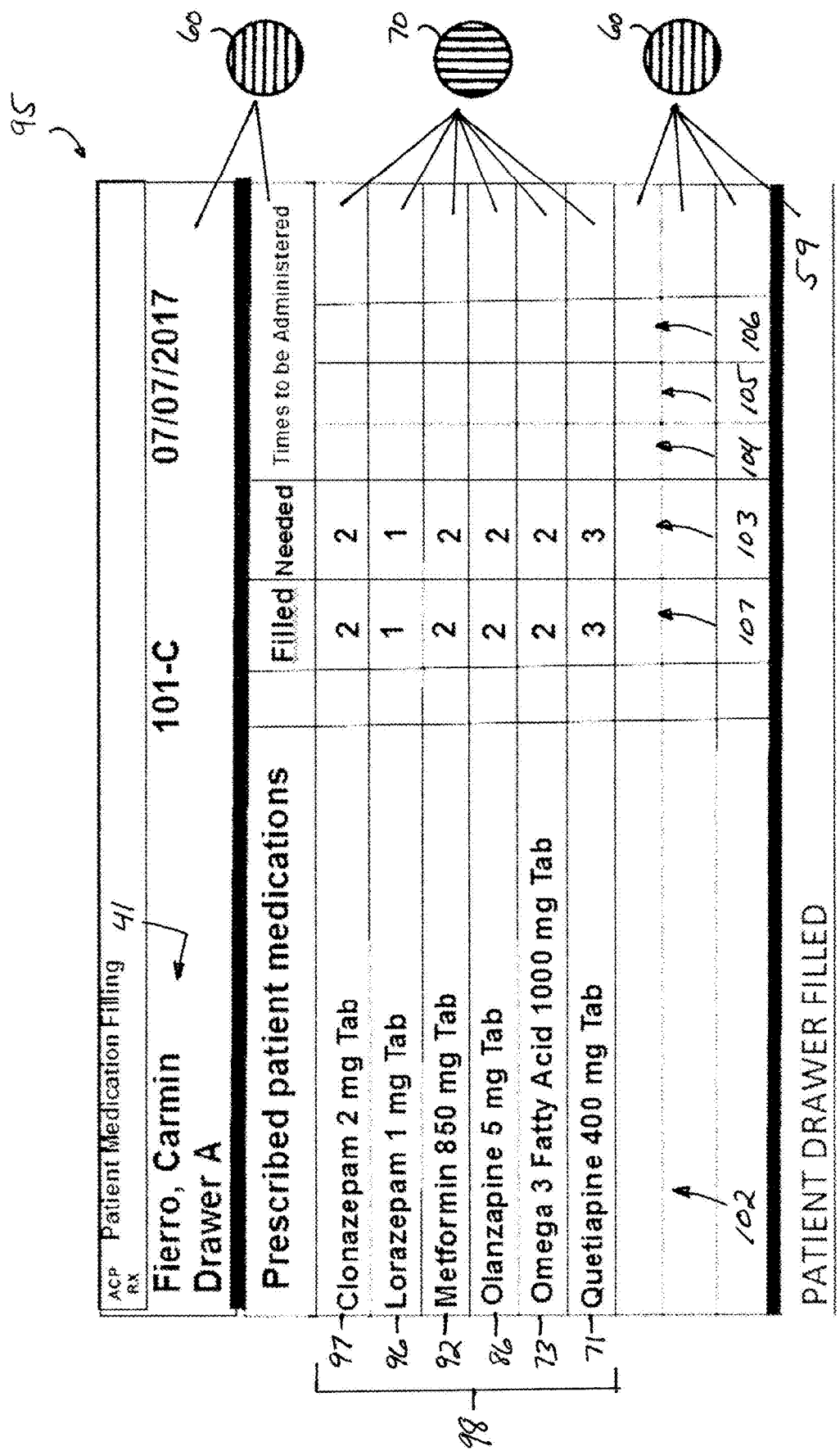

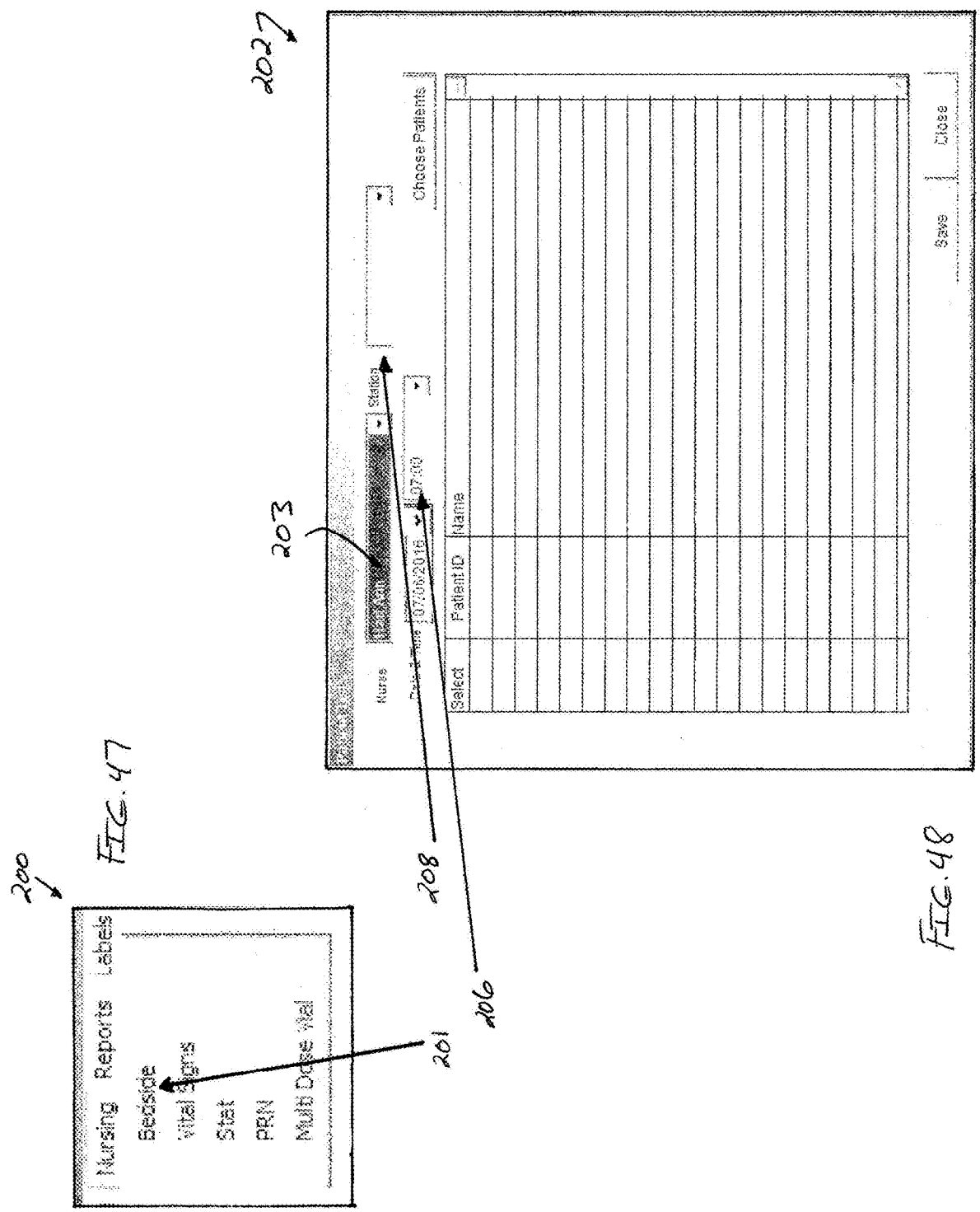

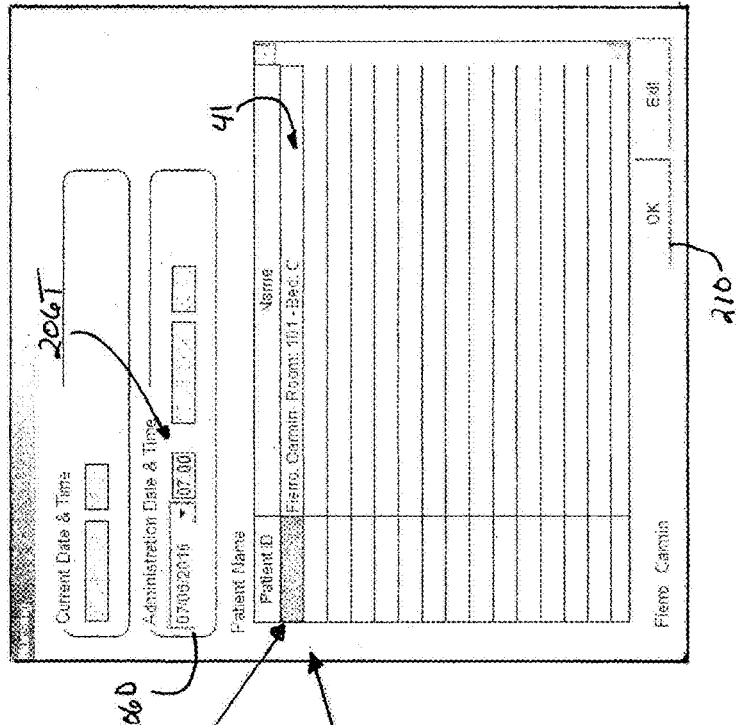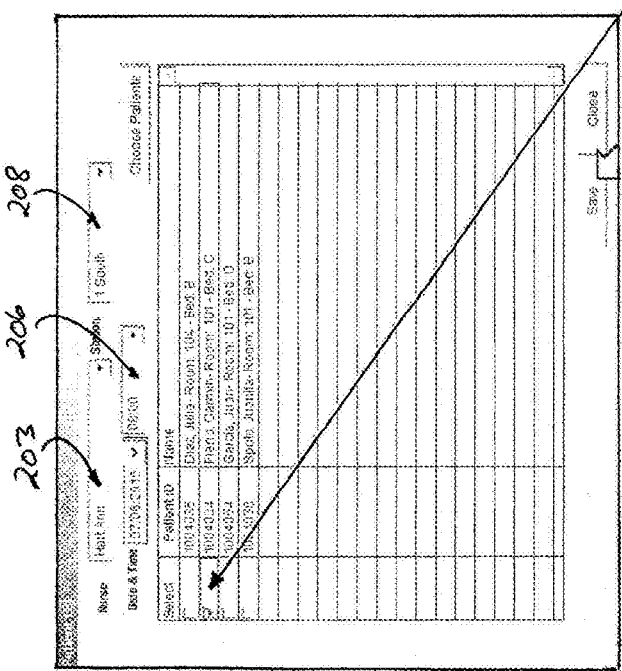

| ACP Nursing | Nurse Medication Administration | | | |
|---|---|---|---|---|
| Fierro, Carmin | Room 101-C | 07/06/2016 | Time: 07:00 - 09:00 | Medications |
| Patient Number 1004034 | | | Birthday: 03/03/1999 | |
| Primary Dr.: Smith, Ben | | Secondary Dr: Rowe, Frank | | |
| Medications Needed | Prescribed Patient Medications below | | | Medications Gathered |
| 1 | Clonazepam 2 mg Tab | | | 0 |
| 1 | Lorazepam 1 mg Tab | | | 0 |
| 1 | Metformin 850 mg Tab | | | 0 |
| 1 | Olanzapine 5 mg Tab | | | 0 |
| 1 | Omega 3 Fatty Acid 1000 mg Tab | | | 0 |
| 1 | Quetiapine 400 mg Tab | | | 0 |
| Gather the above Medications for this Patient for this time period | | | Scan Medications | Exit this Patient |

FIG. 51

FIG. 52

| Nurse Medication Administration | | | | |
|---|---|---|---|---|
| Fierro, Carmin  Room 101-C  Time - 07:00 - 09:00 | | | | |
| Patient Number 1004034  07/06/2016  Birthday: 03/03/1999 | | | | |
| Primary Dr.: Smith, Ben  Secondary Dr: Rowe, Frank | | | | |

| Drugs to be given at this time to the above patient | Times | | Notes area below |
|---|---|---|---|
| | Prescribed | Administered | |
| Clonazepam 2 mg Tab | 08:00  1 | 08:29  0 | |
| Lorazepam 1 mg Tab | 08:00  0 | 08:29  0 | |
| Metformin 850 mg Tab | 08:00  0 | 08:29  0 | |
| Olanzapine 5 mg Tab | 08:00  0 | 08:29  0 | |
| Omega 3 Fatty Acid 1000 mg Tab | 08:00  0 | 08:29  0 | |
| Quetiapine 400 mg Tab | 08:00  0 | 08:29  0 | |

Scan the above medications to be given to this patient so that we know that all the medications are correct before we attempt to administer each medication to the patient

[Scan Medications]  [Exit this Patient]

FIG. 53

Hurse Medication Administration

Fierro, Carmin   Room 101-C   07/06/2016   Time - 07:00 - 09:00   Medications
Patient Number 1004034   Birthday: 03/03/1999
Primary Dr.: Smith, Ben   Secondary Dr: Rowe, Frank Drugs to be given at this time to the above patient

| | Times | | Notes area below |
|---|---|---|---|
| | Prescribed | Administered | |
| Clonazepam 2 mg Tab | 08:00  1 | 08:29  0 | |
| Lorazepam 1 mg Tab | 08:00  1 | 08:29  0 | |
| Metformin 850 mg Tab | 08:00  1 | 08:29  0 | |
| Olanzapine 5 mg Tab | 08:00  1 | 08:29  0 | |
| Omega 3 Fatty Acid 1000 mg Tab | 08:00  1 | 08:29  0 | |
| Quetiapine 400 mg Tab | 08:00  1 | 08:29  0 | |

Scan the above medications to be given to this patient so that we know that all the medications are correct before we attempt to administer each medication to the patient

[Scan Medications]   [Exit this Patient]

FIG. 54

| ACP Nursing Nurse Medication Administration | | | |
|---|---|---|---|
| Fierro, Carmin  Room 101-C  07/06/2016  Time - 07:00 - 09:00  Medications | | | |
| Patient Number  1004034  Birthday: 03/03/1999 | | | |
| Primary Dr.: Smith, Ben  Secondary Dr. Rowe, Frank | | | |

| Drugs to be given at this time range to the above patient | Times | | Notes area below |
|---|---|---|---|
| | Prescribed | Administered | |
| Clonazepam 2 mg Tab | 08:00  1 | 08:29  0 | Note |
| Lorazepam 1 mg Tab | 08:00  1 | 08:29  0 | Note |
| Metformin 850 mg Tab | 08:00  1 | 08:29  0 | Note |
| Olanzapine 5 mg Tab | 08:00  1 | 08:29  0 | Note |
| Omega 3 Fatty Acid 1000 mg Tab | 08:00  1 | 08:29  0 | Note |
| Quetiapine 400 mg Tab | 08:00  1 | 08:29  0 | Note |
| Press "Enter Vital signs" button and enter the vital sign button information | | | Enter Vital Signs  Exit this Patient |

FIG. 56

FIG. 57

Nurse Medication Administration

Fierro, Carmin    Room 101-C    07/06/2016    Time - 07:00 – 09:00    Medications
Patient Number 1004034    Birthday: 03/03/1999
Primary Dr.: Smith, Ben    Secondary Dr.: Rowe, Frank Drugs to be given at this time range to the above patient

| Medication | Times Prescribed | Times Administered | Notes area below |
|---|---|---|---|
| Clonazepam 2 mg Tab | 08:00 / 1 | 08:29 / 0 | Note |
| Lorazepam 1 mg Tab | 08:00 / 1 | 08:29 / 0 | Note |
| Metformin 850 mg Tab | 08:00 / 1 | 08:29 / 0 | Note |
| Olanzapine 5 mg Tab | 08:00 / 1 | 08:29 / 0 | Note |
| Omega 3 Fatty Acid 1000 mg Tab | 08:00 / 1 | 08:29 / 0 | Note |
| Quetiapine 400 mg Tab | 08:00 / 1 | 08:29 / 0 | Note |

Press the "Note" button if the patient does not receive the medication for any reason so that the reason can be entered electronically from a list of known reasons and the reason is automatically added to the patient record.

[Enter Vital Signs]    [Exit this Patient]

FIG. 58

FIG. 59

| ACP Nursing | Nurse Medication Administration | | |
|---|---|---|---|
| Fierro, Carmin | Room 101-C | 07/06/2016 | Time - 07:00 - 09:00 |
| Patient Number 1004034 | | Birthday: 03/03/1999 | |
| Primary Dr.: Smith, Ben | Secondary Dr: Rowe, Frank | | Medications |

Drugs to be given at this time range to the above patient

| | Times | | Notes area below |
|---|---|---|---|
| | Prescribed | Administered | |
| Clonazepam 2 mg Tab | 08:00 | 08:30 | Note |
| | | | Notes |
| | | | Omega 3 Fatty Acid 1000 mg Tab |
| Lorazepam 1 mg Tab | | | Note |
| Metformin 850 mg Tab | | | Note |
| Olanzapine 5 mg Tab | | | Note |
| Omega 3 Fatty Acid 1000 mg Tab | | | Note Patient refused Medication |
| Quetiapine 400 mg Tab | | | Enter Vital Signs / Exit this Patient |

The 'Note' Button beside any drug comes up for the nurse to choose any reason that a medication cannot be given to the patient which becomes part of the patient record. The medication can be given at a later time which will change the patient record.

| ICP Nursing | Nurse Medication Administration | | | |
|---|---|---|---|---|
| Fierro, Carmin | Room 101-C | 07/06/2016 | Time - 07:00 - 09:00 | |
| Patient Number 1004034 | | | Birthday: 03/03/1999 | |
| Primary Dr.: Smith, Ben | | Secondary Dr. Rowe, Frank | Medications | |

| Drugs to be given at this time to the above patient | Times | | Notes area below |
|---|---|---|---|
| | Prescribed | Administered | |
| Clonazepam 2 mg Tab | 08:00 | 08:29 1 | |
| Lorazepam 1 mg Tab | 08:00 1 | 08:29 0 | |
| Metformin 850 mg Tab | 08:00 1 | 08:29 1 | |
| Olanzapine 5 mg Tab | 08:00 1 | 08:29 0 | |
| Omega 3 Fatty Acid 1000 mg Tab | 08:00 1 | 08:29 0 | |
| Quetiapine 400 mg Tab | 08:00 1 | 08:29 0 | |

[ Scan Medications ] [ Exit this Patient ]

FIG. 60

| XCP Nursing | Nurse Medication Administration | | | | |
|---|---|---|---|---|---|
| | Fierro, Carmin | Room 101-C | 07/06/2016 | Time : 07:00 - 09:00 | Medications |
| | Patient Number 1004034 | | | Birthday: 03/03/1999 | |
| | Primary Dr.: Smith, Ben | | Secondary Dr: Rowe, Frank | | |

| Drugs to be given at this time to the above patient | Times | | Notes area below |
|---|---|---|---|
| | Prescribed | Administered | |
| Clonazepam 2 mg Tab | 08:00  1 | 08:29  1 | |
| Lorazepam 1 mg Tab | 08:00  1 | 08:29  1 | |
| Metformin  850 mg Tab | 08:00  1 | 08:29  1 | |
| Olanzapine  5 mg Tab | 08:00  1 | 08:29  1 | |
| Omega 3 Fatty Acid 1000 mg Tab | 08:00  1 | 08:29  1 | |
| Quetiapine  400 mg Tab | 08:00  1 | 08:29  1 | Scan Patient Wristband / Exit this Patient |

FIG. 61

SYSTEM, APPARATUS, AND METHOD FOR DISPENSARY MANAGEMENT

PRIOR HISTORY

This application claims the benefit of U.S. Provisional Patent Application No. 62/366,392 filed in the United States Patent and Trademark Office on 25 Jul. 2016.

FIELD OF THE INVENTION

This disclosure is generally directed to a computer-implemented methodology and application as enabled or supported by way of computer hardware, computer networked systems, and computer accessory systems. More particularly, this disclosure is directed to computer-implemented dispensary-related methodologies and applications for enabling dispensary technicians to achieve more effective and accountable dispensary management generally and dosage tracking particularly.

BRIEF DESCRIPTION OF THE PRIOR ART

Pharmaceutical companies commonly supply/deploy medications to pharmacies/dispensaries by way of blister packs so as to provide unit-dose packaging of requested tablets, capsules or lozenges. Blister packs provide barrier protection for shelf life requirements and provide a certain degree of tamper resistance and thus do provide a significant pharmaceutical protective function. However, processing the blister pack into individual blister pack units is cumbersome as the cavity-separating boundary portions must typically be individually cut with scissors or some similar cutting implement.

Further, medication information is typically provided upon the posterior surfacing of the blister pack such that the information spans large portions of the blister pack and when the individual units are separated from the main body of the blister pack, information becomes degraded and eventually lost to the individual blister pack units. The prior art thus perceives a need for an apparatus that functions to rapidly separate the individual blister pack units and well as a need for re-associating blister pack information to the individual blister pack units as otherwise lost from the separation of units from the blister pack main body.

The prior art further perceives a need for a system and method for more properly managing and tracking unit-doses as they migrate from dispensary to patient and from patient to dispensary in those cases where the unit-doses are not administered to the patient s would be the case in patient refusal or unavailability. Current systems do not provide the kind of security, reporting and tracking enabled by the present invention. The author knows of no existing system that completely tracks and continually monitors the movement of medications from the pharmacy to the nursing areas or to the patient bedside or other areas and warns the nurse, and pharmacy personnel or other health care people when there is a potential mistake.

A typical hospital in the United States only uses a scanned barcode or machine readable code approach for medications on the nursing or dispensing side for enhancing dosage management. In addition, state of the art systems for nursing mainly use one of several pieces of information associated with any given medication to prevent a medication error. Typically, for example, a nursing side code scanning system will utilize the national medication code which is a part of the UPC code as an identification of the medication. No current system scans code information for the purpose of cross-checking expiration dates, lot numbers and tracking numbers. Also no presently practiced system uses an approach characterized by scanning coded medications at the pharmacy or dispensary area.

Another problem the industry faces is medication theft from the stream of moving medications. No present system tracks medication from its dispensary or pharmacy source through to patient administration. By failing to track tracking when medications leave the pharmacy, who put medications in a patient drawer, when the medication was delivered to the nursing area, when a nurse makes contact with a patient, when did the nurse take the blood pressure and pulse etc., when a nurse removes the medications from the patient drawer, and when a nurse ends contact with the patient, present systems create greater opportunity for theft of medications as they move through the hospital setting.

Needless to say, errors in the administration of medication within a hospital setting can have devastating effects on a patient and his or her family. The author, for example, recalls an instance in which a baby died in a local hospital from incorrectly administered medication. The hospital was found liable and forced to pay millions of dollars in compensatory damages to the family. The prior art perceives a need for an enhanced system and method for dispensary management, and one that tracks movement of medications from source to delivery by providing a code-based information check points at every stop along the way as addressed by these specifications and summarized in more detail hereinafter.

SUMMARY OF THE INVENTION

The distribution of medications within hospital type settings is thus of critical importance and multiple layers of machine readable codes associated with the various medications and the scanning of these codes as they move from and to each point in the distribution process is central to the practice of the present invention. The present invention further provides color coding and optional, but preferred audio warning systems that are key to the proper deployment and use of the system. Color coding and audible alerts for use in the pharmacy and nursing software sides are very important to help the employees quickly and immediately take an awareness of mistakes or problems within the system. Those manning the pharmacy people and attending to patients must react quickly to not allow a medication error or an incorrect medication movement to go unrecognized.

The present system inherently tracks medication codes, expiration date, lot number, and tracking number and all movements of the medications when they leave the pharmacy to when they are administered to the correct patients or returned to the system if not used. The present system further maintains records of the medication movement from the beginning of the medication distribution process to the end of the process or return to the system if not used. The present system and method were thus developed to help prevent medication dispensing errors during the distribution of medications from a central pharmacy to the nursing area where the medications are given to patients.

The author further notes that when individual blister pack units are separated from the information concerning the contained medication, the opportunity for errors to occur in the distribution process is increased. By associating the individual blister pack units with barcodes or other machine-readable codes linked to an information database, the individual blister pack units may thus be better managed and tracked within a medication distribution stream. A further object of the present invention is thus to both provide better information for each blister pack unit and to also better track the movement of medications from the pharmacy in a safe, secure method.

For example, the disappearance of medications is unfortunately prevalent. Given the convoluted pathways through which medications often pass, the opportunity for theft from the medication distribution steam is significant. This means that in many cases, medications do not arrive at a patient who otherwise is in desperate need for the medication. It is well known that many mistakes occur and that millions of medications are stolen every year in both United States hospitals as well as foreign hospitals. A primary objective according to the present invention is to dramatically help eliminate medication theft and errors in medication delivery.

The present system reports when medications are filled in the pharmacy, the technician who filled the medications, alerts the pharmacy when a medication it is trying to fill for a patient is incorrect, expired, over-filled, under-filled, and identifies to the precise second, if desired, when each medication is filled in the pharmacy, leaves the pharmacy, arrives at the nursing station, etc. The system provides information concerning when a dispensing person or nurse has made contact with the patient, how much time the nurse has spent with the patient, if the patient refuses to take any of the medications and why, how to track medications if a patient does not receive the medication, and where it returns to for tracking reasons, etc.

To achieve these and other readily apparent objectives, the present invention basically contemplates a computerized dispensary management system and method for enhancing dispensary product management at a pharmacy or similar other type dispensary. The system and method are supported by a blister pack separation apparatus for speeding the provision of individual blister pack units to the dispensary via cumbersome blister packs otherwise typically requiring manual separation via a cutting action. The relatively more rapid provision of a series of individual blister pack units as separated from a bulk dose blister pack further enables barcoding capabilities for each of the blister pack units so that each may be better managed or tracked within the dispensing system.

The computerized dispensary management system according to the present invention may be said to essentially comprise a non-transitory, computer-implementable application for implementing the dispensary management system according to certain proprietary dispensary system management rules and protocol built upon or around the use of a basic filler screenshot. At least one application-implementing computer implements the non-transitory, computer-implementable application and is in communication with a scanner system for scan-inputting product-identifying barcode or other machine-readable code information and patient- or customer- or person-identifying barcode or other machine-readable code information to the non-transitory, computer-implementable application for further processing.

The person-identifying barcode or other machine-readable code information is scanned or read for inputting information about an associated person to identify that person alongside a product regimen prescribed or ordered for the person as would be the case for a daily medication or prescription regimen. The non-transitory, computer-implementable application is structured to provide a series of sequential screenshots based upon a basic filler screenshot for filler side product management and for guiding the user through the regimen-filling process. The regimen-filling process is believed characterized by screenshot re-arrangements that visually and dynamically occur upon or to the basic filler screenshot as each successive product barcode or other machine-readable code is scanned or read. The screenshot re-arrangements, so characterized, are believed to enhance dispensary product management at least insofar as a computer program tracks and accounts for each scanned product associated with any given person or patient.

The basic filler screenshot comprises a series of row sections and a series of column sections for visually tabulating information concerning the personal product regimen as prescribed. The series of row sections enable a multiple product listing in a first column section, a scanned product entry column, a maximum product prescription column, and at least one, but preferably a plurality of time slot columns. A time-based information piece (e.g. 08:00) in a select time slot column is removed when the new or successive product or machine readable code is scanned, which time-based information piece coincides with an iterative number added to the scanned product entry column.

A plurality of time slot columns preferably extend in adjacency to one another, and when a time-based information piece is removed from the select time slot column, it shifts to an adjacent time slot column. The time-based information piece, when removed from the select time slot column, is preferably shifted to an adjacent time slot column nearer to or in the direction of the scanned product entry column then bearing a select iterative number. In this manner, the shifting of visual manner upon the screenshot in a direction of iterative number additions, provides for a robust medication filling process for each scanned medication.

The basic filler screenshot further preferably comprises a primary background coloration. The primary background coloration changes to a secondary, product-filled coloration in a select row section when the iterative number in the select row section matches a maximum product prescription number in the maximum product prescription column for the select row section. In other words, when all time-based information pieces are withdrawn from the time slot column sections, the row section for that product has been filled and the row section changes to a secondary color in contrast to the primary color thereby providing a further visual cue that the select medication has been properly filled at the dispensary.

The basic filler screenshot may further preferably comprise a message row section for displaying a visual alert when a scanned product error is detected. Noting that the basic filler screenshot preferably comprises a primary background coloration, the primary background coloration may preferably change to a tertiary, product-error coloration in the message row section when the scanned product error is detected. An audible alert may be further and preferably provided when the scanned product error is detected for enhancing or bolstering the visual alert otherwise provided in the message row section.

As prefaced above, the computerized dispensary management system according to the present invention may embrace usage of a blister pack separation apparatus for speeding blister pack separation into individual blister pack units for further processing. The blister pack separation apparatus according to the present invention may be said to comprise a substantially rigid, incompressible support base; a blister pack-corralling boundary portion; a resilient, compressible cavity-field bedding portion; and at least one, but typically a plurality of blade element(s).

Each blade element extends upwardly from the support base orthogonal thereto, and the bedding portion is positioned in adjacency to the at least one blade element atop the support base for compressibly receiving anterior portions of a blister pack cavity field of a blister pack. The boundary portion surrounds the bedding portion and the blade element(s) for corralling at least one blister pack as supported by the bedding field. Each blade element is configured for cutting through cavity-separating boundary portions of the blister pack when directed thereagainst under an externally applied force. The bedding portion is compressible during the externally applied force and resiliently returnable when the externally applied force is removed from the blister pack thereafter being separated into individual blister pack units. The individual blister pack units are then associated with product-identifying or machine readable code information, and thereby rendered scannable via the scanner system for inputting the product-identifying or machine readable code information to the non-transitory, computer-implementable application for further processing.

The blister pack separation apparatus according to the present invention allows medication blister cards mostly used internationally to be quickly cut up into single unit doses blister to rapidly be separated instead of being manually cut with scissors. This is often done in international markets because the medications in areas outside the United States are typically not available as labeled unit dose medications as otherwise is the case in the United States. When the international blister cards are cut up with scissors, most times the individual blister pack units do not have identification or only have some identification but not all the required identification. The blister pack separation apparatus rapidly cuts these blister cards so that they can be easily packaged with a packaging/labeling machine with all the correct information including the barcodes as described in these specifications. The blister pack separation apparatus basically helps the unit dose distribution process go faster.

A second phase of the system concerns a dispenser side or nursing side of product management as opposed to the filler side or pharmacy side of product management. In this regard, the computerized dispensary management system and method according to the present invention provide a basic dispenser screenshot. The basic dispenser screenshot comprises a series of dispensing row sections for each listed product. The dispensing row sections each terminate at a bifurcated upper and lower window arrangement or segment.

Together the upper and lower windows of the bifurcated segment(s) provide at least a first dispensing column section characterized by column-alternating upper and lower windows and overlapped with the listed row sections. The basic dispenser screenshot may also preferably comprise the primary background coloration that changes to a secondary, product-dispensed coloration when a product item is correctly dispensed and an iterative number is added to a select window as selected from the upper and lower windows of the bifurcated terminal segment.

The blister pack separation apparatus, it will be recalled, speeds blister pack separation into individual blister pack units and preferably comprises a substantially rigid, incompressible support base; a blister pack-corralling boundary portion; a resilient, compressible cavity-field bedding portion; and at least one blade element. The blister pack-corralling boundary portion is also preferably resiliently compressible or actuable during application of the externally applied force and resiliently returns when the externally provided or applied force is removed therefrom.

The blister pack separation apparatus may further preferably comprise a plurality of blade elements whereby the bedding portion extends intermediate at least two of the plurality of blade elements. The blister pack separation apparatus may further preferably comprise a relaxed bedding portion height at the bedding portion and a relaxed boundary portion height at the boundary portion. The relaxed boundary portion height is greater than the relaxed bedding portion height thereby providing a relaxed apparatus depth in adjacency to the blade element(s).

The blister pack separation apparatus cooperates with blister pack(s) having a blister pack depth or height. The blister pack depth or height is greater than the relaxed apparatus depth. Thus, the posterior portion of the blister pack is raised relative to the boundary portion when supported anteriorly by the bedding portion. The blister pack separation apparatus may further preferably comprise a substantially rigid, incompressible cover element for covering the blister pack and interfacing between the blade element(s) and the source of the externally applied force for protecting the source of the externally applied force from damage via the blade element(s).

Viewed methodologically, the present invention may be said to provide a computerized dispensary management method for enhancing dispensary product management comprising the steps of: providing a non-transitory, computer-implementable application for visually prompting a user via a visual display in communication with at least one application-implementing computer; and prompting the user with a basic filler screenshot upon the visual display for filler side product management and inputting data to be processed by the non-transitory, computer-implementable application and the at least one application-implementing computer.

The method may be said to further comprise the step of scan-inputting person-identifying or machine readable code information via a scanner system in communication with the non-transitory, computer-implementable application and the at least one application-implementing computer; identifying a personal product regimen associated with the person-identifying or machine readable code information; and displaying the personal product regimen upon the visual display via the basic filler screenshot.

The basic filler screenshot preferably comprises a maximum product regimen number as set forth in a first column section and a scanned product entry number as set forth in a second column section. At least one product or machine readable code associated with the displayed personal product regimen is scan-input for adjusting the basic filler screenshot with an iterative number in the second column section. The personal product regimen may thus be filled when the maximum product regimen number matches the scanned product entry number as incrementally adjusted via the iterative number.

The computerized dispensary management method further contemplates the basic filler screenshot having a series of row sections and a series of column sections for visually tabulating information associated with the personal product regimen, such that the series of row sections enable a multiple product listing in a first column section, a second scanned product entry column, a third maximum product prescription column, and at least one time slot column. The step of removing a time-based information piece from the time slot column of a select row section when a successive new product or machine readable code is scanned is contemplated.

The withdrawn information piece coincides with an iterative number, which iterative number is added to the scanned product entry column of the select row section. Recalling that a plurality of time slot columns may preferably extend in adjacency to one another, the information piece, when removed from the select time slot column, is preferably shifted to an adjacent time slot column. The information piece, when removed from the select time slot column, is preferably shifted to an adjacent time slot column in the direction of the scanned product entry column.

Recalling that the basic filler screenshot preferably comprises a primary background coloration, the method may be said to further preferably comprise the step of changing the primary background coloration to a secondary, product-filled coloration in the select row section when the iterative number in the select row section matches a maximum product prescription number in the maximum product prescription column. Further, the method contemplates the steps of (s) displaying a visual alert in a message row section of the basic filler screenshot when a scanned product error is detected, and (b) changing the primary background coloration to a tertiary, product-error coloration in the message row section when the scanned product error is detected. An audible alert may also be provided when the scanned product error is detected for bolstering the visual alert.

The computerized dispensary management method may still further preferably comprise the step of providing a basic dispenser screenshot via the non-transitory, computer-implementable application. The basic dispenser screenshot operates for dispenser side product management, and comprises a series of dispensing row sections for listing each product as earlier filled. The dispensing row sections each preferably terminate at a bifurcated upper-lower window segment.

The bifurcated upper-lower window segments together provide at least a first dispenser column section characterized by column-alternating upper and lower windows overlapped with the dispensing row sections. The primary background coloration of the basic dispenser screenshot may preferably change to a secondary, product-dispensed coloration when a product item is correctly dispensed and an iterative number is added to a select window as selected from the bifurcated upper-lower window arrangement or segment.

The blister pack separation apparatus is believed to support certain preliminary steps of the dispensary management method, including the steps of: separating a blister pack into individual blister pack units via a blister pack separation apparatus substantially as earlier described and associating the separate individual blister pack units with product-identifying or machine readable code information. The product-identifying or machine readable code information is scannable via the scanner system for inputting the product-identifying or machine readable code information to the non-transitory, computer-implementable application for processing.

BRIEF DESCRIPTIONS OF THE DRAWINGS

Other features of the invention will become more evident from a consideration of the following brief descriptions of illustrations submitted in support of the subject invention:

FIG. No. 1 is a first anterior or frontal plan view of a generic prior art blister pack having a 4×2 arrangement of individual product-containing cavities or pockets.

FIG. No. 2 is a first side elevational view of the generic prior art blister pack otherwise depicted in FIG. No. 1.

FIG. No. 3 is a first posterior or rear plan view of the generic prior art blister pack otherwise depicted in FIG. Nos. 1 and 2, the posterior plan view showing a textual message placed upon the rear surfacing and spanning the length and width of the prior art blister pack.

FIG. No. 4 is a second anterior or frontal plan view of the generic prior art blister pack having a 4×2 arrangement of individual product-containing cavities or pockets with broken or dotted lines depicting cut lines at cavity-separating boundary portions for separating the generic blister pack into individual blister pack units.

FIG. No. 5 is a second side elevational view of the generic prior art blister pack depicting cut lines at cavity-separating boundary portions for separating the generic blister pack into individual blister pack units.

FIG. No. 6 is a second posterior or rear plan view of the generic prior art blister pack depicting the individual blister pack units separated from one another at the cavity-separating boundary portions, the unified textual message placed upon the rear surfacing and spanning the length and width of the prior art blister pack becoming broken during the cutting process.

FIG. No. 7 is a top plan view of a generic blister pack separation apparatus according to the present invention.

FIG. No. 8 is a side elevational view of a generic blister pack separation apparatus according to the present invention with parts broken away to depict three 4×2 blister packs received and supported by the blister pack separation apparatus.

FIG. No. 9 is a top view of the generic blister pack separation apparatus according to the present invention as otherwise depicted in FIG. No. 8 showing the three 4×2 blister packs received and supported by the blister pack separation apparatus.

FIG. N. 10 is an enlarged, sequentially first side view depiction of the blister pack separation apparatus according to the present invention with parts broken away to depict the structural relationship between the blister pack separation apparatus and three 4×2 blister packs received and supported upon the blister pack separation apparatus in a relaxed state or configuration.

FIG. No. 11 is an enlarged, sequentially second side view depiction of the blister pack separation apparatus according to the present invention with parts broken away to depict the structural relationship between the blister pack separation apparatus and three 4×2 blister packs received and supported upon the blister pack separation apparatus in a relaxed state or configuration with a top cover board or cover element or cover element being directed into placement atop the posterior portions of the three 4×2 blister packs.

FIG. No. 12 is an enlarged, sequentially third side view depiction of the blister pack separation apparatus according to the present invention with parts broken away to depict the structural relationship between the blister pack separation apparatus and three 4×2 blister packs received and supported upon the blister pack separation apparatus during compression or actuation via downwardly directed forces for simultaneously separating all individual blister pack units from the parent blister packs.

FIG. No. 12A is an enlarged, fragmentary sectional view as enlarged and sectioned from FIG. No. 12 to depict in greater detail the cutting or separation action at a cavity-separating boundary portion.

FIG. No. 13 is an enlarged, sequentially fourth side view depiction of the blister pack separation apparatus according to the present invention with parts broken away to depict the structural relationship between the blister pack separation apparatus and a series of individual blister pack units supported upon the blister pack separation apparatus as returned to the relaxed state or configuration with the top cover board or cover element or cover element being removed therefrom.

FIG. No. 14 is a diagrammatic depiction of a preferred blister pack separation apparatus arrangement according to the present invention supporting three blister packs being directed toward a compressive force-providing arrangement for separating the three blister packs into individual blister pack units.

FIG. No. 15 is a diagrammatic depiction of an alternative blister pack separation apparatus arrangement according to the present invention supporting three blister packs being directed toward a compressive force-providing arrangement for separating the three blister packs into individual blister pack units.

FIG. No. 16 is a diagrammatic depiction of the preferred blister pack separation apparatus arrangement according to the present invention holding three blister packs and being directed through the compressive force-providing arrangement for separating the three blister packs into individual blister pack units.

FIG. No. 16A is an enlarged, fragmentary sectional view as enlarged and sectioned from FIG. No. 16 to depict in greater detail the cutting or separation action at a cavity-separating boundary portion.

FIG. No. 17 is a diagrammatic depiction of the alternative blister pack separation apparatus arrangement according to the present invention holding three blister packs and being directed through the compressive force-providing arrangement for separating the three blister packs into individual blister pack units.

FIG. No. 17A is an enlarged, fragmentary sectional view as enlarged and sectioned from FIG. No. 17 to depict in greater detail the cutting or separation action at a cavity-separating boundary portion.

FIG. No. 18 is a diagrammatic depiction of a series of barcode-bearing sleeves or packs receiving a series of individual blister pack units and being rotated to show anterior and posterior sides of the barcode-bearing sleeves or packs containing the series of individual blister pack units.

FIG. No. 19 is a frontal elevational view of a first drawer-holding cassette ensemble depicting a 2×4 arrangement of patient drawers held by the drawer-holding cassette ensemble, each patent drawer being outfitted with a patient-identifying barcode.

FIG. No. 20 is a top plan view of a patient drawer removed from a drawer-holding cassette ensemble to depict a series of drawer compartments or sections, and each drawer compartment or section holding barcoded contents.

FIG. No. 21 is a frontal elevational view of a second drawer-holding cassette ensemble depicting a 3×2 arrangement of patient drawers held by the drawer-holding cassette ensemble, each patent drawer being outfitted with a patient-identifying barcode.

FIG. No. 22 is a depiction of an identification badge for a dispenser person, the identification badge bearing a dispenser-identifying barcode.

FIG. No. 23 is a depiction of a small tablet container, the small tablet container bearing a product-identifying barcode.

FIG. No. 24 is a depiction of a small consumable liquid container, the small consumable liquid container bearing a product-identifying barcode.

FIG. No. 25 is a depiction of a needle assembly, the needle assembly bearing a product-identifying barcode.

FIG. No. 26 is a depiction of an individual blister pack unit-containing pack, the individual blister pack unit-containing pack bearing a product-identifying barcode.

FIG. No. 27A is a diagrammatic depiction of a simple scanner system scanning a product-identifying barcode borne by a small consumable liquid container.

FIG. No. 27B is a frontal depiction of the second drawer-holding cassette ensemble again depicting the 3×2 arrangement of patient drawers with a lower right patient drawer being extended for receiving the scanned small consumable liquid container otherwise depicted in FIG. No. 27A.

FIG. No. 28 is a diagrammatic depiction of a simple scanning system scanning a patient-identifying barcode of an extended patient drawer as otherwise depicted in FIG. No. 27B for inputting patient-identifying data and prompting the display of a patient general information window upon a visual display in communication with a computer-based network as supported or enabled by a non-transitory, computer-implementable, dispensary-management software application according to the present invention.

FIG. No. 29 is a List of Patient Medications screenshot provided by the non-transitory, computer-implementable, dispensary-management software application according to the present invention, the List of Patient Medications screenshot being prompted via the patient general information window.

FIG. No. 30 is a Patient General Information window provided by the non-transitory, computer-implementable, dispensary-management software application according to the present invention, the Patient General Information window for prompting the screenshot otherwise depicted in FIG. No. 29.

FIG. No. 31 is a Drawer A type Patient General Information window provided by the non-transitory, computer-implementable, dispensary-management software application according to the present invention, the Drawer A type Patient General Information window for prompting the screenshot otherwise depicted in FIG. No. 29.

FIG. No. 32 is a Drawer B type Patient General Information window provided by the non-transitory, computer-implementable, dispensary-management software application according to the present invention, the Drawer B type Patient General Information window for prompting the screenshot otherwise depicted in FIG. No. 29.

FIG. No. 33 is a table depicting the alternating nature of Drawer A versus Drawer B relative to days of the week for a given patient.

FIG. No. 34 is a Scan Medications Not Used from Previous Day screenshot provided by the non-transitory, computer-implementable, dispensary-management software application according to the present invention, the Scan Medications Not Used from Previous Day screenshot being reflective of the List of Patient Medications screenshot.

FIG. No. 35 is a first sequential Basic Filler screenshot provided by the non-transitory, computer-implementable, dispensary-management software application according to the present invention, the Basic Filler screenshot being central to practice of the dispensary management system supported by the non-transitory, computer-implementable, dispensary-management software application for filling a scan-input product order or regimen and before any product has been scan-input into the system.

FIG. No. 36 is a second sequential Basic Filler screenshot provided by the non-transitory, computer-implementable, dispensary-management software application according to the present invention after a first product unit (of twelve total product units according to the product order or regimen) has been scan-input into the system.

FIG. No. 37 is a third sequential Basic Filler screenshot provided by the non-transitory, computer-implementable, dispensary-management software application according to the present invention after a second product unit has been scan-input into the system.

FIG. No. 38 is a fourth sequential Basic Filler screenshot provided by the non-transitory, computer-implementable, dispensary-management software application according to the present invention after a third product unit has been scan-input into the system.

FIG. No. 39 is a fifth sequential Basic Filler screenshot provided by the non-transitory, computer-implementable, dispensary-management software application according to the present invention after a fourth product unit has been scan-input into the system.

FIG. No. 40 is a sixth sequential Basic Filler screenshot provided by the non-transitory, computer-implementable, dispensary-management software application according to the present invention after a fifth product unit has been scan-input into the system.

FIG. No. 41 is a seventh sequential Basic Filler screenshot provided by the non-transitory, computer-implementable, dispensary-management software application according to the present invention after a sixth and a seventh product unit has been scan-input into the system.

FIG. No. 42 is an eighth sequential Basic Filler screenshot provided by the non-transitory, computer-implementable, dispensary-management software application according to the present invention after an eighth product unit has been scan-input into the system.

FIG. No. 43 is a ninth sequential Basic Filler screenshot provided by the non-transitory, computer-implementable, dispensary-management software application according to the present invention after a ninth product unit has been scan-input into the system.

FIG. No. 44 is a tenth sequential Basic Filler screenshot provided by the non-transitory, computer-implementable, dispensary-management software application according to the present invention after a tenth product unit has been scan-input into the system.

FIG. No. 45 is an eleventh sequential Basic Filler screenshot provided by the non-transitory, computer-implementable, dispensary-management software application according to the present invention after an eleventh product unit has been scan-input into the system.

FIG. No. 46 is a twelfth eleventh sequential Basic Filler screenshot provided by the non-transitory, computer-implementable, dispensary-management software application according to the present invention after a twelfth and final product unit has been scan-input into the system.

FIG. No. 47 is a depiction of a drop down menu window for initiating a dispensing side of the non-transitory, computer-implementable, dispensary-management software application according to the present invention.

FIG. No. 48 is a pre-populated patient list screen of the non-transitory, computer-implementable, dispensary-management software application according to the present invention, the pre-populated patient list screen being prompted via the bedside function button of the drop down menu otherwise depicted in FIG. No. 47.

FIG. No. 49 is a populated patient list screen of the non-transitory, computer-implementable, dispensary-management software application according to the present invention, the populated patient list screen being prompted via the bedside function button of the drop down menu otherwise depicted in FIG. No. 47.

FIG. No. 50 is a select patient screen of the non-transitory, computer-implementable, dispensary-management software application according to the present invention, the patient list screen being selected from the populated patient list screen otherwise depicted in FIG. No. 49.

FIG. No. 51 is a drawer contents list screenshot of the non-transitory, computer-implementable, dispensary-management software application according to the present invention, the drawer contents list screenshot providing a list of unit-doses for the given patient for a given time slot.

FIG. No. 52 is a first sequential Basic Dispenser screenshot of the non-transitory, computer-implementable, dispensary-management software application according to the present invention after a first of the six unit-doses has been gathered and scan-input at the bedside for administration.

FIG. No. 53 is a second sequential Basic Dispenser screenshot of the non-transitory, computer-implementable, dispensary-management software application according to the present invention after six of the six unit-doses has been gathered and scan-input at the bedside for administration.

FIG. No. 54 is a first depiction of a third sequential Basic Dispenser screenshot of the non-transitory, computer-implementable, dispensary-management software application according to the present invention before a patient-identifying barcode or machine readable code is scan-input at the bedside for unit-dose administration.

FIG. No. 55 is a second depiction of the third sequential Basic Dispenser screenshot of the non-transitory, computer-implementable, dispensary-management software application according to the present invention with a patient information window pop-up appearing in front of the third sequential Basic Dispenser screenshot before a patient-identifying barcode or machine readable code is scan-input at the bedside for unit-dose administration.

FIG. No. 56 is a first depiction of a fourth sequential Basic Dispenser screenshot of the non-transitory, computer-implementable, dispensary-management software application according to the present invention prompting the user to enter Vital Signs information at the bedside before unit-dose administration.

FIG. No. 57 is a second depiction of the fourth sequential Basic Dispenser screenshot of the non-transitory, computer-implementable, dispensary-management software application according to the present invention with a Vital Signs information window pop-up appearing in front of the fourth sequential Basic Dispenser screenshot at the bedside before unit-dose administration.

FIG. No. 58 is a third depiction of a fourth sequential Basic Dispenser screenshot of the non-transitory, computer-implementable, dispensary-management software application according to the present invention prompting the user to enter Notes information at the bedside before unit-dose administration.

FIG. No. 59 is a third depiction of the fourth sequential Basic Dispenser screenshot of the non-transitory, computer-implementable, dispensary-management software application according to the present invention with a Notes information window pop-up appearing in front of the fourth sequential Basic Dispenser screenshot at the bedside before unit-dose administration.

FIG. No. 60 is a fifth sequential Basic Dispenser screenshot of the non-transitory, computer-implementable, dispensary-management software application according to the present invention after a first of the six unit-doses has been administered and scan-input at the bedside.

FIG. No. 61 is a sixth sequential Basic Dispenser screenshot of the non-transitory, computer-implementable, dispensary-management software application according to the present invention after six of six unit-doses has been administered and scan-input at the bedside.

DETAILED DESCRIPTION OF THE PREFERRED SYSTEM, APPARATUS, AND METHOD

Referring now to the drawings with more specificity, the present invention preferably provides an electronic, computer-based dispensary management system and method for enhancing dosage tracking and accountability. The electronic, computer-based dispensary management system and method according to the present invention are believed further supported by a blister pack separation or processing apparatus and methods whereby individual doses, otherwise provided by way of bulk blister pack delivery packaging, are separated, packaged into machine-readable coded sleeves, and scanned into the electronic, computer-based dispensary management system and method for enhancing tracking and accountability of the individual unit-doses.

A blister pack is generally depicted and referenced at 10 and is a generic term for several types of pre-formed packaging typically used for packaging relatively small consumer goods, foods, and commonly for pharmaceuticals or medications. The primary component of a blister pack is a cavity or pocket field 11 made from a formable web, usually a thermoformed plastic. This cavity or pocket field 11 usually has a piercable backing 12 of paperboard, aluminum foil, or plastic.

Received in the individual cavities or pockets 13 of the cavity or pocket field 11 are small products such as consumer goods, foods, or pharmaceuticals as at 14. The anterior layer (i.e. cavity or pocket field 11) and posterior layer (i.e. piercable backing 12) of a blister pack 10 are thus useful for protecting the small, cavity-enclosed products (e.g. pharmaceuticals 14) against external factors, including humidity and contamination, for extended periods of time, and further provide an economical method of small product delivery to the consumer. Blister packaging is notably a particularly common packaging method for medication delivery outside the United States where medications are commonly unavailable as labeled unit dose medications.

Comparatively referencing FIG. Nos. 1-3, the reader will there consider a generic blister pack as at 10 housing small products such as small consumer goods, foods, or pharmaceuticals as at 14. The blister pack 10 comprises an anterior cavity or pocket field 11 preferably made from a formable web, such as thermoformed plastic. The anterior cavity or pocket field 11 comprises a series of cavity or pocket formations as at 13 in which cavity or pocket formations 13 the small products exemplified by pharmaceuticals or medications 14 are received. The cavity or pocket formations 13 are closed or covered by a substantially planar, piercable, posterior backing material as at 12. The posterior backing material 12 may preferably be outfitted with certain marking material so as to provide a user with readable information as at generic textual information 15 pertaining to the cavity or pocket-enclosed products 14.

In the case of pharmaceuticals, the information 15 provided upon the posterior packaging material 12 is very often provided across the entire span of the posterior backing material 12 such that when individual cavities or pocket formations 13 and the corresponding section of posterior backing material 12 are separated from the blister pack 10 by cutting (as diagrammatically depicted at scissors 100), the information 15 borne by a select section of posterior backing material 12 tends to embrace only a portion of the information 15 otherwise provided upon the posterior backing material 12, and is thus ineffective at conveying to the user or reader the necessary information otherwise borne by the entire span of posterior backing material 12.

In this regard, the reader will comparatively consider FIG. Nos. 4-6, and FIG. No. 6 particularly. FIG. No. 4 depicts the beginning process of hand-cutting 100 or separating individual blister pack units 16 from the blister pack 10 from an anterior plan view with separation lines being shown in broken lining 101. FIG. No. 5 depicts a blister pack in edge view with separation lines being shown in at the lining 101. FIG. No. 6 depicts individual blister pack units 16 completely separated from one another after cutting 100 with spaces 102 therebetween and thus showing a separated blister pack 10' with the posterior backing material 12 of individual blister pack units 16 failing to individually convey the entire textual message otherwise appearing as at full information message 15 depicted in FIG. No. 3 with only part of the fully information message being borne by each individual blister pack unit 16 upon sections 26.

Individual blister pack units as at 16 thus comprise (a) a section of the anterior cavity or pocket field 11 comprising the individual cavity or pocket formation 13, (b) a section 26 of the posterior backing material 12, and (c) the small, cavity-enclosed or pocket-enclosed product exemplified by a pharmaceutical, medication, or unit-dose as at 14. As indicated, the individual blister pack units 16 are typically separated manually as by cutting with a scissors as at 100 or by way of manually tearing perforated seams (not specifically illustrated).

The presently described systems and methods contemplate a blister pack separation apparatus as at 17 that is processed (i.e. pressed as at force vector arrows 120) to more rapidly separate the individual blister pack units 16 from the main bodies of blister pack(s) 10. Each blister pack separation apparatus 17 according to the present invention is specifically configured to simultaneously separate individual blister pack units 16 from a blister pack 10 in whatever form the blister packs 10 are initially provided. The blister pack 10 shown in the drawings submitted in support of these specifications each comprise 8 individual blister pack units 16 arranged in a rectangular 4×2 arrangement. Notably, blister packs are provided in a wide variety of shapes and arrangements and each apparatus 17 according to the present invention is specifically built for a given type of arrangement.

Nevertheless, it is believed that the blister pack separation apparatus 17 according to the present invention, of whatever configuration, universally comprises the same set of features, and in this regard preferably comprises a substantially rigid, incompressible support bottom or base as at 18; a resilient, compressible blister pack-corralling boundary portion as at 19; a resilient, compressible cavity field bedding portion as at 20; and at least one, but typically a plurality of blade elements as at 21 configured for cutting through cavity-separating boundary portions 22 of the blister pack(s) 10 when directed thereagainst under the action of an externally applied pressure or force as diagrammatically depicted at force vector arrows 120.

In this regard, it is contemplated that the blister pack separation apparatus 17 according to the present invention may be directed through an apparatus for imparting the pressure or force diagrammatically depicted by force vector arrows 120 such as opposed fixed axis (rotating 140) drums as at 121 spaced apart a distance 123 substantially equal to but slightly less than the distance 124, which distance 124 is a fully compressed, blister-cutting distance provided by the blister pack separation apparatus 17 and system according to the present invention.

The reader will note from a consideration of FIG. No. 12 that resilient, compressible blister pack-corralling boundary portion 19 and resilient, compressible cavity field bedding portion 20 are preferably resilient formations that resiliently actuate or compress as at 125 under pressure or force(s) 120 directed thereinto for driving the anterior cavity or pocket field 11 layer and posterior backing material 12 into fixed or stationary blades 21 for driving the cutting edges 23 therethrough to separate individual blister pack units 16 from the blister pack(s) 10. When forces 120 are removed, the resilient, compressible blister pack-corralling boundary portion 19 and resilient, compressible cavity field bedding portion 20 resiliently return as at 126 to a relaxed state generally and comparatively depicted in FIG. Nos. 10, 11, 13, 14, and 15.

When in the relaxed state generally and comparatively depicted in FIG. Nos. 10, 11, 13, 14, and 15, the blister pack separation apparatus 17 generally has a relaxed height as generally depicted and referenced at relaxed height 127 for the blister pack separation apparatus 17 outfitted with an optional top cover board or cover element 24, and generally depicted and referenced at relaxed height 128 for the blister pack separation apparatus 17 without a top cover board or cover element 24. Referencing FIG. Nos. 10, 11, 13, 14, 15, the reader will there note the top plane 129 of the resilient, compressible blister pack-corralling boundary portion 19 is parallel to the top plane 130 of the posterior backing material 12 when the blister pack(s) 10 are supported upon the resilient, compressible cavity field bedding portion 20 when in the relaxed state such that the depth 131 of the of the cavity-receiving portion of the blister pack separation apparatus 17 in the relaxed state is preferably less than the thickness 132 of the blister pack(s) 10, and thus the posterior backing portion 12 sits above the top plane 130 when in the relaxed state.

When pressed or compressed via forces 120, the blister pack separation apparatus 17 drives the posterior backing portion 12 toward the blade tip(s) 23 via the compressibility of the resilient, compressible blister pack-corralling boundary portion 19 and resilient, compressible cavity field bedding portion 20. Comparatively referencing FIG. Nos. 14-17A, the reader will more particularly consider the optional inclusion of the top cover board or cover element 24. Top cover board or cover element 24 essentially functions to protect the mechanism imparting the pressure or forces 120 from damage via the blade tip(s) 23 given that the spacing at 123 is slightly less than the spacing 124. Referencing FIG. Nos. 12A and 16A the reader will note a slight superficial cut 25 to the top cover board or cover element 24 during the pressing process here described. The spacing 133 is thus essentially equal to the spacing 123 less the thickness 134 of the top cover board or cover element 24 and slightly less than the thickness 135.

The present invention thus embraces and contemplates an apparatus-based blister pack separation process whereby multiple blister packs 10 may be apparatus-received and positioned atop bedding portions 20 with boundary portions 22 in superior adjacency to cutting blades 22 arranged or configured within the perimeter of a resilient, compressible blister pack-corralling boundary portion 19 and intermediate or extending through a resilient, compressible cavity field bedding portion 20. Blade elements 21 function to sever a multiplicity of individual blister pack units 16 from the main body of the blister packs 10 under high force scenarios as generally depicted in FIG. Nos. 12, 16, and 17.

The multiplicity of individual blister pack units 16, when severed from the main body of the blister pack 10, are often lacking in complete information provided upon the individual sections 26 of the posterior backing material 12 as generally depicted in FIG. No. 6. The present system and method contemplates next outfitting each individual blister pack unit 16 with barcoded or machine-readable coded information linked to a database or individual unit-dose profile so that a full field of small product information may thus be linked to each individual blister pack unit 16 via the barcode or machine readable code as at 28.

To most easily outfit each individual blister pack unit 16 with the barcode or machine readable code information 28, it is contemplated that each individual unit 16 may be inserted into or received in (as at arrow 141) a barcode-outfitted or machine readable-outfitted sleeve or pack 27 as generally depicted in FIG. No. 18. Rotating arrows 142 depict the barcode-outfitted sleeves or packs 27 with the received individual blister pack units 16 being rotated to show rear or posterior pack side and front or anterior pack sides. Once received in the sleeve or pack 27 outfitted with product-identifying barcode or machine readable code information 28, each individual blister pack unit 16 may thus be properly linked to information associated with the small product exemplified by a pharmaceutical 14 via the product-identifying barcode or machine readable code 28 outfitted upon the anterior surfacing of the pack 27.

It will thus be seen that the system and method according to the present invention is based upon barcoding or similar other coding process such as matrix coding, which coding is preferably of two-dimensional type so that the coding is of a sufficient quality and character to adequately support information linkage to not only the national medication code (i.e. part of the UPC code as an identification of the medication), but also code information for the purpose of cross-checking expiration dates, lot numbers and tracking numbers.

The preferred two-dimensional coding is thus preferably and essentially outfitted upon all or most structures that move within the distribution stream of the system so that better tracking information and accountability can be achieved within or according to the system and method. The importance of better tracking information and accountability cannot be overstated in the context of medicine delivery to patients within hospital or similar other settings as noted above. The health and welfare of patients within such settings is of utmost importance and the more effective the systems and methods practiced within such settings, the better the quality of life for patients and their caretakers generally.

Each patient within such a setting is typically or commonly associated with or assigned to a patient drawer as at 30 within a lockable cassette ensemble 29 housing a multiplicity or plurality of patient drawers 30 as generally depicted and referenced in FIG. No. 19. According to the system and method of the present invention, each patient drawer 30 is preferably outfitted with a patient barcode or machine readable code 31 linked to a patient database for identifying or providing patient-identifying profile information for each patient. Further, each article housed within the patient drawer 30 is preferably outfitted with barcode or machine readable code information as at product-identifying barcode or machine readable code information 28.

Referencing FIG. No. 20, it will be seen that every item, location, and container must be barcoded or outfitted with machine-readable code as at 28 for the system and method to work efficiently and accurately. FIG. Nos. 19 through 21 depict a series of individual patient drawers 30 in which medications or medicinal items are housed. All drawer-housed items, such as unit-containing sleeves 27, pill containers 32, needle assemblies 33, and liquid containers 34, are outfitted with product-identifying barcode or machine readable code information 28 and code-scanned to ensure that the items inserted into the drawers 30 are correct items for the patient associated with the drawer 30, including information regarding the correct dosage for any particular medication, and that the mediation is not expired. Every drawer 30 is thus monitored for contents by way of the system and method according to the present invention.

FIG. No. 27B depicts a patient drawer 30 in an extended state as at 35 relative to a lockable cassette ensemble 29 and FIG. No. 27A depicts a simple barcode or machine readable code scanner 111 scanning 110 a code-bearing liquid container 34 before the same is placed into the extended state patient drawer 35 for enhancing the tracked condition of the code-bearing liquid container 34. Comparatively referencing FIG. Nos. 20 and 27B, the reader will further note that each patient drawer 30 may be preferably divided into sections 36 with divider walls separating the sections 36. The sections 36 are typically divided by time of day for delivery of section contents to each individual patient.

When the patient-identifying barcode or machine readable code 31 is scanned as generally depicted in FIG. No. 28 at scan 110 via scanner 111, the non-transitory, computer-implementable software application according to the present invention receives the scan-input information and thereby prompted to display the screenshot generally depicted and referenced in FIG. No. 28 at 38 upon a visual display 39 in communication with a computer 40 or computing network as at 50. Screenshot 38 is a general information screenshot for any given patient as generally referenced at patient name 41, and further references a patient drawer identifier 42, a drawer action directive section as at 43, an unreturned fill dates and times information bar as at 44, a proposed fill date and times category including proposed starting date and time information bars as at section 45, and proposed ending date and time information bars as at section 46 with an optional number of intervening days feature as at 47.

When the user clicks on the OK tab 48 of screenshot 38, the user is prompted with screenshot 49 upon the visual display 39 in communication with the computer 40 or computing network 50. Screenshot 49 depicts a listing of patient medications or medications indicator or message as at row section 92, a listing of pharmaceutical medications as at column section 113, and a total quantity of pharmaceutical medications for each medication listed in column section 113 as set forth in column section 112. Comparatively referencing FIG. Nos. 29 and 30, the reader will note that the patient general information window 38 in FIG. No. 30 depicts a "Fill Only" function 51 in the drawer action directive section 43, which prompts the screenshot 49 depicted in FIG. No. 29. FIG. Nos. 29 and 30 thus depict the initial visual prompts in the form of window 38 and screenshot 49 utilized to fill the patient drawer 30 for the first time.

Referencing screenshot 38, the reader will note that the drawer letter(s) A (or B or C) as at patient drawer identifier 42 are arbitrary letters that are part of a barcode or machine readable code including the patient number, (e.g. ~9), and the drawer letter that was assigned to the first drawer for a given patient which is typically the letter A. The first patient drawer 30 is typically initially filled with a 24 hour supply of medications for that patient. The filled patient drawer 30 is typically sent out so as to provide the patient 41 with his or her first medication doses that will be given on the second shift at the hospital.

However, if the patient 41 is admitted much earlier in the day, a special supply of medications may be prepared including a 24 hour supply plus any additional hours that may be required before the second shift starts. The time 15:30 set forth in screenshot 38 as at 52 is a time set by the customer/hospital and represents the deadline by which the medications must be delivered to the nursing wing on which the patient 41 then resides. Section 45 of screenshot 38 references the date and time medications are to be delivered to the patient 41 within the hospital (via the patient drawer 30), and section 46 references the date and time the patient drawer 30 is to be returned from the patient 41.

Thus, for a new patient receiving their medications on a Monday, for example, the patient drawer identifier 42 would be the letter A given for the first time as passed onto the second shift staff. The listing of medications otherwise set forth in screenshot 49 are thus required to be placed into the patient drawer 30 and delivered to the patient location before the second shift begins, typically at 3:00 pm. A patient "Drawer B" in contrast to Drawer A will start to be used Tuesday afternoon. The medication set forth in the column section 113 may not be exactly the same for Drawer A versus Drawer B for Monday versus Tuesday because a physician may have prescribed a different medication regimen for Tuesday, and/or discontinued a medication that was prescribed for Monday.

Thus, the letters of the patient drawer identifier 42 continuously interchange back-and-forth. Drawer A for a patient will represent a 24 hour supply of medications for patient Carmen Fierro. Drawer A will stay in the medication cart until the exchange patient Drawer B arrives on Tuesday which represents the next 24 hours supply of medications for Carmen Fierro. This changing back-and-forth from Drawer A to drawer B goes on as long as the patient stays in the hospital. The terms "Return and Fill" as at 53 of drawer action directive section 43 will always be on the screen if the patient is still part of the system and has not checked out or died. The first patient drawer with a 24 hour supply of medications is normally the A drawer. The next drawer, Drawer B, is exchanged with Drawer A every 24 hours as comparatively depicted in FIG. Nos. 31 through 33.

Comparatively referencing FIG. No. 31 versus FIG. No. 32, the reader will consider that when the user scans an "A" patient drawer barcode or machine readable code 31 for cassette filling, the patient drawer 30 comes up as the A Drawer as at screenshot 38 in FIG. No. 31. Each patient drawer 30 has a barcode or machine readable code label 31 beginning with a number and letter sequence 55 (e.g. 9A . . . ) followed by the patient or customer ID number 56 (e.g. . . . 1004054). This sequence indicates this is a patient drawer 30 requiring to be filled with the next 24 hour supply of medications. Referencing FIG. No. 32, the patient drawer 30 is a returning drawer as at 54 of section 43 with a previous 24 hour supply of medications. The screenshot 38 in FIG. No. 32 depicts a patient drawer 30 being returned to the pharmacy or dispensary. The screenshot 38 in FIG. No. 31 is checked "Return and Fill" as at 53 because this patient 41 is scheduled to stay another day in the hospital.

Referencing screenshot 38 in FIG. No. 32, the reader will there see a B Drawer as at section 42. The B Drawer is being returned to the pharmacy area to be checked and closed since the patient is not returning for another day because the software does not see any medications for another day, or that patient has already checked out. Normally, each patient's drawer 30 is filled for 24 hours or a one day supply. However, occasionally the pharmacy may fill the patient drawer 30 for a 2-day or a 3-day supply, especially if the pharmacy is closed over the weekend or closed for a holiday.

FIG. No. 33 depicts the changing or recycling of the drawer letters 57 on a daily basis and changing back and forth from Drawer A on the first day to Drawer B on the second day to Drawer A on the third day, etc. The first day on Monday is the Drawer A is filled with a 24 hour supply of medications and sent out as the first 24 hour supply of medications for patent drawer 30 associated with 9A1004034. The next day (Tuesday), a second patient drawer 30, Drawer B, is filled and then exchanged for the original Drawer A which returned to the pharmacy. The exchanging goes back and forth until the patient 41 leaves the hospital. The letters could be other letters and sometimes be three different letters for a patient 41, but the exchanging of patient drawers 30 in this manner continues the same way. The use of three different letters occurs when the pharmacy may be closed over the weekend when the pharmacy may be closed for one or two days.

FIG. No. 34 depicts a screenshot 58 indicating a scenario when certain medications have not been consumed or used. When the patient drawer 30 is returned from the previous day, the pharmacy will first check to see if any medications are remaining in the patient drawer 30. If so, the pharmacy technician will scan 110 any remaining medications which will allow giving a credit to the patient 41 since the returned medication was not given to the patient 41. In screenshot 58, the reader will thus see a Scan Medications Not Used message as at message row section 59. FIG. No. 34 further attempts to introduce a background color scheme for consideration by the reader. The reader will note that a drawing symbol indicating initial blue coloration 60 is indicated in FIG. No. 34 for at least all row sections bearing a listed medication type.

Screenshot 61 in FIG. No. 35 depicts a Basic Filler screenshot according to the present invention. Screenshot 61 is a patient screen listing the types of medicines to be gathered as set forth in column section 102, the maximum prescribed quantity of each medicine gathered for placement in the patient drawer 30 are indicated in maximum product prescription column section 103, dose delivery times are indicated in time slot column sections 104, 105, and 106, and a doses filled or scanned product entry column section 107. As earlier indicated, the patient drawer 30 may preferably be divided into sections 36 that correspond to time of day and also correspond with time slot column sections 104, 105, and 106. The message row section 59 bears the message, "Scan New Medications for the Next 24 Hours Exchange".

The reader will note that the doses filled or scanned product entry column section 107 contains an all zero (0) count on screenshot 61. Further, the number of time slot column sections corresponds to the number of doses required for each medication in the column section 103. Drawing symbol indicating initial blue coloration 60 is also indicated in FIG. No. 35 for all row sections bearing a medication where the row number set forth in the column section 107 does not match the row number set forth in the column section 103 and time slot(s) do appear in each of the column sections 104, 105, and 106.

Stated another way, the various medications set forth in column section 102 are now ready to be barcode- or machine readable code-scanned 110 as they are being placed or entered into the patient drawer 30. Noting that the column of zero's (0's) in column section 107 represents that no medications have yet been scanned 110 or entered into the patient drawer 30, the column of numbers in column section 103 to the right of the column section 107 shows the total quantity of medications requiring placement into the patient drawer 30. The next column sections 104, 105 and 106 to the right of column section 103 provide the times of day each medication should be given and which part of the drawer (divided by time for each medication) should be given to the patient 41. The number of time entries in the time slot column sections 104, 105, and 106 corresponds to the total numbers of medications required for any given medication listed in column section 102.

Screenshot 62 as set forth in FIG. No. 36 generally depicts the patient screen as it is being filled for the first time. Comparatively referencing FIG. No. 35 versus FIG. No. 36, the reader will note that each time a medication or code-bearing pack 27 is scanned 110, a "time" indicator (e.g. reference 14:00 at window 63 in FIG. No. 35) for that particular medication disappears as at full window 63 in screenshot 61 versus empty window 63 in screenshot 62. An iterative number (i.e. +1 and e.g. 0+1=1) appears in another window 64 in column section 107 within the row section for the listed medication indicating the item or dose has been added to the patient drawer 30.

In other words, for the first medication scanned, the number "One" (1) appears in the column section 107 to replace the "Zero" (0) otherwise there appearing. Further, the 20:00 time as at window 65 disappears from column section 104, and the times 08:00 appearing in column section 105 and 14:00 appearing in column section shift one column left into column sections 104 and 105 respectively thereby emptying window 63 and moving closer visually to column section 107. The total number of medications set forth in column section 103 remains the same and represents the correct amount of each medication line or quantity of medications to be placed or entered into the patient drawer 30.

Screenshot 62 in FIG. No. 36 and screenshot 66 in FIG. No. 37 comparatively depict a second "time" disappearing as at full window 67 in screenshot 62 versus empty window 67 in screenshot 66 with an iterative number being added to the window 64 (e.g. 1+1=2), and a left-shift of the time 14:00 from column section 105 in screenshot 62 to column section 104 in screenshot as the 08:00 time slot is filled for Quetiapine 400 mg Tab. In other words, the number "2" then appears in the column section 107. Screenshot 66 in FIG. No. 37 and screenshot 68 in FIG. No. 38 comparatively depict a third "time" disappearing as at full window 65 in screenshot 66 versus empty window 65 in screenshot 68, with an iterative number being added to the window 64 (e.g. 2+1=3).

Referencing FIG. No. 38 and screenshot 68, the reader will note that the row numbers "3" in column sections 107 and 103 match one another thereby indicating the correct quantity of Quetiapine 400 mg Tab(s) has been scanned and entered into the patient drawer 30. When the particular medication quantity is complete for a given medication, the particular row section or line for a listed medication within section 102 preferably changes color as indicated at drawing symbol indicative of "pink" coloration as at 70. The "pink" coloration drawing symbol 70 is directed to the entire row section for Quetiapine 400 mg Tab. The change in coloration from blue 60 to pink 70 further visually indicates to the person filing the patient drawer 30 that the item or medication has been completely filled.

If a fourth dose of Quetiapine 400 mg Tab were now to be scanned, or a Quetiapine 1000 mg Tab were now to be scanned, a warning or alert would be provided in message row section 59 to visually indicate that an incorrect item, dose, or medicine is scanned for the given patient 41. The warning message or alert at message row section 59 may preferably appear along with a preferred but optional audible signal (e.g. a buzz sound) for alerting the person filling the patient drawer 30 of the potential mistake or incorrectly attempted entry of medication to the patient drawer 30.

In other words, noting that the number in window 64 matches the number in window 69 in FIG. No. 38; further noting that the time entries from empty windows 65, 67, and 63 have been removed; and still further noting the change in coloration at row section 71 from blue 60 to pink 70, it is evident from the patient screenshot 68 that the dosage for Quetiapine 400 mg Tab has been completely and properly filled. However, if the person filling the patient drawer 30 does attempt to overfill the drawer 30 with this particular medication, a warning or alert message may appear at message row section 59 which may preferably be coupled with an audible alarm. Similarly, throughout the filling process, if an item is incorrect, not completely filled, overfilled, expired, etc., a warning message and audible alert will come up to warn the person filling the patient drawer 30 that a mistake is about to happen.

The foregoing process is essentially repeated for each medication that is to be placed into the patient drawer 30. Referencing FIG. No. 39, the reader will there consider screenshot 72 and will compare screenshot 72 to screenshot 68 in FIG. No. 38. Further referencing row section 73 for Omega 3 Fatty Acid 1000 mg Tab, the reader will see that 2 doses are required as at window 74, and when the first of two (2) required doses is scanned 110, a first time identifier is withdrawn as at full window 75 in screenshot 68 versus empty window 75 in screenshot 72 with the 08:00 time slot medication being shifted from column section 105 to column section 104; and an iterative number (e.g. 0+1=1) appears in window 77 replacing the zero (0) otherwise previously there appearing.

Screenshot 78 depicts a second of two (2) Omega 3 Fatty Acid 1000 mg doses being scanned 110, the time identifier being comparatively removed from full window 79 in screenshot 72 versus empty window 79 in screenshot 78; and an iterative number (e.g. 1+1=2) appears in window 77. The Omega 3 Fatty Acid 1000 mg Tab dosage of row section 73 for this day is then complete comparing the maximum dosage indicated in column section 103 at window 80 to doses filled column section 107 at window 77. Thus row section 73 becomes highlighted in pink coloration 70 building upon the pink coloration 70 also highlighting row section 71.

Referencing FIG. No. 41 and the screenshot 81 there depicted, the reader will see that both doses of Olanzapine 5 mg Tab(s) have already been scanned 110 into the system. The doses entered number at window 82 in column section 107 matches the maximum doses number at window 83 in column section 103; all time slots have disappeared from windows 84 and 85 (comparing windows 84 and 85 in FIG. No. 40); and the row section 86 for Olanzapine 5 mg Tab has been highlighted in pink coloration 70 as compared to the blue coloration 60 otherwise previously appearing in FIG. No. 40.

FIG. No. 42 depicts screenshot 87 with a first of two (2) doses of Metformin 850 mg Tabs having been scanned 110 into the system as at row section 92. Comparing FIG. No. 41 of screenshot 81 to FIG. No. 42 of screenshot 87, the reader will there see that a time identifier is removed from full window 88 in screenshot 81 versus empty window 88 in screenshot 87; an iterative number is added to window 89; and the time 08:00 otherwise previously appearing in 88 of column section 105 in screenshot 81 shifts to window 90 of column section 104 in screenshot 87.

FIG. No. 43 depicts screenshot 91 with a second of two (2) doses of Metformin 850 mg Tabs having been scanned 110 into the system as at row section 92. Comparing FIG. No. 42 of screenshot 87 to FIG. No. 43 of screenshot 91, the reader will there see that a time identifier is removed from full window 90 in screenshot 87 versus empty window 90 in screenshot 91; an iterative number is added to window 89; and the time 08:00 otherwise previously appearing in window 90 of column section 104 in screenshot 87 is withdrawn from window 90 of column section 104 in screenshot 87. Pink coloration 70 thus highlights row section 92.

Screenshots 93, 94, and 95 comparatively and sequentially depict the Lorazepam 1 mg Tab supply as at row section 96 and Clonazepam 2 mg Tab supply as at row section 97 being scanned and entered into the patient drawer 30. Screenshot 93 depicts the doses entered number of row section 96, column section 107 matching the maximum doses number of row section 96, column section 103 with pink coloration highlighting row section 96 and all time slots having been removed from row section 96, column section 104. Screenshots 93, 94, and 95 further comparatively depict a first and second of two (2) Clonazepam 2 mg Tabs or doses being scanned into the patient drawer 30 with the time identifiers in column sections 104 and 105 being sequentially shifted to the left as the two doses are scanned 110 and entered into the patient drawer 30.

Referencing FIG. No. 46, the reader will note that all the numbers in column section 107 match the numbers in column section 103 when viewed in side-by-side relation; pink coloration dominates the medication listing field or block 98 of row sections 71, 73, 86, 92, 96, and 97; and all time indicators are withdrawn from column sections 104, 105, and 106. The reader will note that the block 98 of rows 71, 73, 86, 92, 96, and 97, highlighted in pink coloration 70, is preferably sandwiched between upper and lower layers of blue coloration 60. These arrangements indicate the patient drawer 30 is completely filled with scanned 110 and entered medications, and an additional visual alert message may be provided in the message row 59 indicating that the patient drawer 30 is completely filled.

Once the patient drawer 30 is delivered to the patient location, the items located within the patient drawer 30 or drawer contents may be dispensed to the patient 41 according to the time schedule generally set forth in the time slot column sections 104, 105, 106 and patient drawer sections 36. From a drop down menu 200 provided by the software application according to the present invention generally depicted in FIG. No. 47, the dispensing person 203 (typically a nurse) may chooses a bedside function as at prompt 201, which bedside function prompt 201 prompts a pre-populated patient/customer list screen 202 as generally depicted in FIG. No. 48.

The pre-populated patient/customer list screen 202 is populated with patients/customers assigned to the dispensing person 203 who is properly identified via an identification tag 204 with dispenser barcode or similar other machine readable code 205 as generally depicted and referenced in FIG. No. 22. A group of patients assigned to dispensing person 203 is thus listed on the patient/customer list screen 202 per a dispensing date and time as at 206. Thus, a list 207 of potential patients/customers is provided from which list 207 the dispensing person 203 may choose a patient or customer as further comparatively depicted in FIG. Nos. 49 and 50. The dispensing person 203 may further designate which station 208 to which he or she is then assigned.

When a patient or customer is chosen or selected from the patient/customer list screen 202, an Administration Date and Time screen 209 is provided as generally depicted in FIG. No. 50. The Administration Date and Time screen 209 bears the patient/customer name 41 and patient/customer ID as at 56, as well as the Administration Date as at 206D and Administration Time as at 206T. By confirming the correct patient/customer and administration date/time aspects via clicking or pressing the OK button prompt 210, a drawer contents or items list screenshot 211 appears as generally depicted in FIG. No. 51. When prompted via the contents list screenshot 211, the dispenser person 203 may press or click on the "Scan Medications" button 212.

The reader will note that a unit-dose corresponding with the selected time slot and the iterative number appears in column section 213, and a list of the unit-dose types is presented in column section 214 with column section 215 indicating whether the unit-doses have been collected. At this stage, zero (0) unit-doses have been collected for administration as generally depicted in column section 215. The reader will further consider that the screenshot 211 comprises the primary background coloration as exemplified by blue coloration 60 in all row sections at this juncture.

When the Scan Medications tab 212 is selected, a new screenshot 216 then appears as generally depicted in FIG. No. 52. The screenshot 216 lists the drawer items or contents in a columnar manner in column section 223 alongside a combination Times column section 217 comprising a Prescribed Time column section 218 and an Administered Time column section 219. Both the Prescribed Time column section 218 and the Administered Time column section 219 comprise a combination or bifurcated terminal row section, segment or arrangement 220 for each medication or drawer item to be dispensed, and includes an upper time slot window as at 221 and a lower scanned item entry window as at 222.

A dropdown is optionally available to display all the prescribed medications otherwise set forth in the column section 223 in the event a certain drawer content or item does not have a barcode or machine readable code or there is a problem with an unreadable barcode or unreadable similar other code for any given drawer item. In this case, the drawer item may be chosen via the dropdown. Notably, the preferred method is to scan the barcode or machine readable code information rather than relying upon the optional dropdown method here discussed. The process of scanning items for patient administration may then begin.

Referencing FIG. No. 52 the reader will there see that when a drawer item is correctly scanned, the row section for the scanned medication along with the bifurcated terminal row section 220 at column section 218 (comprising upper time slot window 221 and lower scanned item entry window 222) turns or changes to a secondary, item-gathered coloration exemplified by pink coloration 70 from the otherwise primary background coloration exemplified by blue coloration 60. If the item for the time slot has already been chosen, is incorrect, is expired, or any other error occurs, a message may preferably appear in the message row section 59, and preferably turn or change to a tertiary coloration (e.g. red) in contrast to the primary background coloration.

The process of scanning or inputting iterative drawer items may thus continue. Each time an item is scanned, the row section for the particular item scanned along with the upper and lower windows 221 and 222 within the bifurcated terminal section or section 220 within column section 218 preferably changes to the secondary coloration (e.g. pink coloration 70) thereby visually signaling the dispensing person 203 that the item scan process for any gathered given item from the listing in column section 223 is then complete as generally depicted in screenshot 224.

FIG. No. 54 depicts screenshot 225. The reader will consider row sections 226 setting forth the drawer content listing 223, inclusive of the bifurcated terminal segments 220 with upper and lower windows 221 and 222 of column section 218 that together define a content-gathered block as at 227. Column section 219 and Notes column section 233 together represent an administration block 234. Administration block 234 preferably comprises the primary background coloration at this juncture as generally and comparatively depicted in FIG. Nos. 54 and 56. When content-gathered block 227 has completely been changed to the secondary coloration exemplified by pink 70, the dispensing person 203 is provided with a message indicating this development within the message row section 59, and prompted with a Scan Patient Wrist Band prompt as at 228. Notably, state of the art practices require that the patient or customer be outfitted with a coded wristband or a patient-local barcode or machine readable code for identifying the patient at the bedside.

A second message prompt or overlay window 230 is then provided as in FIG. No. 55 and the dispensing person 203 may proceed to scan the coded wristband or patient-local barcode or machine readable code. An error message may appear if an incorrect patient/customer barcode or machine readable code is then scanned. If such an error message is displayed, the dispensing person must locate the correct patient/customer via the wristband barcode or machine readable code or patient-local code methodology. Once the correct patient/customer is located, the time is registered and is incorporated into the patient/customer record. Other options for a given patient/customer may be further provided.

Referencing screenshot 235 in FIG. No. 56, for example, the reader will there consider, for example, an "Enter Vital Signs" prompt button 231. If such "Enter Vital Signs" prompt button 231 is selected, an information entry or input portal or window overlay 232 may be provided for inputting the patient's/customer's Vital Signs as generally depicted in FIG. No. 57. Further, if any of the scannable drawer/section 36 items for a given time slot require notations, a notation feature may be provided as at Note tab(s) 236 in column section 233.

By pressing or clicking on a Note tab 236 for a given row section 226, a note input portal or window 237 is provided as generally depicted in FIG. No. 59. A number of different common occurrences are listed in input portal or window 237, and selection thereof can be entered into the patient/customer record by pressing the "Save & Close" tab 238. An exemplary "Patient Refused Medication" note 239 has been added to the patient record for Omega 3 Fatty Acid 1000 mg Tab row section 226 in FIG. No. 59.

Further referencing FIG. No. 59, the reader will there consider that the drawer/section item for the 08:00 Omega 3 Fatty Acid 1000 mg Tab was not to be administered to the patient for the noted reason of Patient Refused Medication. This item, as originally scanned as gathered, but not administered, must be returned to the original patient drawer 30 source. In such a case, the patient drawer 30 is again scanned. If an incorrect patient drawer is scanned, an error message appears. Returning items that have been correctly matched with the proper patient drawer 30 source are indicated as such via the secondary coloration (e.g. pink coloration 70). When the items have been scanned/inputted as returned to the correctly matched patient drawer 30 source, the row section for each returning patient/drawer item returns to the primary background coloration (e.g. blue coloration 60).

FIG. Nos. 60 and 61 comparatively depict the process of timely administration of the listed drawer contents of row sections 226. If the drawer contents are timely administered according to the date/time 206 prescription as at 206D and 206T, the terminal bifurcated segment 220 for that row section 226 will change from the primary background coloration (e.g. blue coloration 60) to a secondary dose-administered coloration (e.g. pink coloration 70) within column section 219. FIG. No. 60 thus depicts a migration of pink coloration into the column section 219 when the unit-dose of Clonazepam 2 mg Tab is administered. When all unit-doses have been timely administered the Administration column section 219 changes from the primary background coloration to the secondary, dose-administered coloration that preferably supplements and matches the coloration of the gathered-block 227.

While the foregoing specifications set forth certain specificity, the same should not be construed as setting forth limits to the invention but rather as setting forth certain preferred systemic aspects, embodiments, and methodologies. The present invention basically contemplates a computerized dispensary management system and method for enhancing dispensary product management as supported by a blister pack separation apparatus that speeds the provision of individual blister pack units to the dispensary for further management once outfitted with cooperative barcoding.

The computerized dispensary management system according to the present invention may be said to essentially comprise a non-transitory, computer-implementable application for implementing the dispensary management system according to certain proprietary dispensary system management rules and protocol built upon the use of a basic filler screenshot. At least one application-implementing computer implements the non-transitory, computer-implementable application and is in communication with a scanner system for scan-inputting product-identifying barcode or machine readable code information and patient- or customer- or person-identifying barcode or machine readable code information to the non-transitory, computer-implementable application for further processing.

The person-identifying barcode or machine readable code information (as at barcode or machine readable code 31) is scanned for inputting information about an associated person (e.g. a patient) to identify that person alongside a product regimen prescribed or ordered for the person as would be the case for a daily medication regimen as generally depicted in FIG. No. 29, 34, and 35. The non-transitory, computer-implementable application is structured to provide a series of sequential screenshots based upon a basic filler screenshot as exemplified by the initial screenshot depicted in FIG. No. 35 for filler side product management and for guiding the user through the regimen-filling process. The regimen-filling process is believed characterized by screenshot re-arrangements that visually and dynamically occur upon the basic filler screenshot as each successive product barcode or machine readable code 28 is scanned. The screenshot re-arrangements, so characterized, are believed to enhance dispensary product management at least insofar as a computer program tracks and accounts for each scanned product associated with any given person or patient.

The basic filler screenshot comprises a series of row sections as variously referenced at 59, 71, 73, 86, 92, 96, and 97, and a series of column sections as variously referenced at 102, 103, 104, 105, 106, and 107 for visually tabulating information concerning the personal product regimen as prescribed. The series of row sections enable a multiple product listing in a first column section as at 102, a scanned product entry column as at 107, a maximum product prescription column as at 103, and at least one, but preferably a plurality of time slot columns as at 104, 105, and 106. A time-based information piece (e.g. 08:00) in a select time slot column is removed when the new or successive product barcode or machine readable code 28 is scanned, which time-based information piece coincides with an iterative number that is added to the scanned product entry column 107.

Noting that a plurality of time slot columns preferably extend in adjacency to one another, the reader will recall that the time-based information piece, when removed from the select time slot column, is shifted to an adjacent time slot column. For example, the 14:00 time-based information piece shifts from column section 106 to column section 105 in comparative screenshots 61 and 62. The time-based information piece, when removed from the select time slot column, is shifted to an adjacent time slot column nearer to or in the direction of the scanned product entry column 107 then bearing a select iterative number. In this regard, the reader will note that the 14:00 information piece draws nearer the iterative number presentation set forth in column section 107 across screenshots 61, 62, and 66, and thus visually draws the user's eye toward the completion state as successive products are scanned into the system.

The basic filler screenshot further preferably comprises a primary background coloration as at blue coloration 60. The primary background coloration changes to a secondary, product-filled coloration exemplified by pink coloration 70 in a select row section when the iterative number in the select row section matches a maximum product prescription number in the maximum product prescription column for the select row section. In other words, when all time-based information pieces are withdrawn from the column sections 104 through 106, the row section for that product has been filled and the row section changes to a secondary color in contrast to the primary color.

The basic filler screenshot may further preferably comprise a message row section as at 59 for displaying a visual alert when a scanned product error is detected. Noting that the basic filler screenshot preferably comprises a primary background coloration, the primary background coloration may preferably change to a tertiary, product-error coloration (e.g. green) in the message row section when the scanned product error is detected. An audible alert may be further and preferably provided when the scanned product error is detected for enhancing or bolstering the visual alert otherwise provided in the message row section 59.

The computerized dispensary management system may embrace usage of a blister pack separation apparatus as at 17 for speeding blister pack 10 separation into individual blister pack units 16 for further processing. The blister pack separation apparatus 17 according to the present invention may be said to comprise a substantially rigid, incompressible support base as at 18; a blister pack-corralling boundary portion as at 19; a resilient, compressible cavity-field bedding portion as at 20; and at least one, but typically a plurality of blade element(s) as at 21.

The at least one blade element 21 extends upwardly from the support base 18 orthogonal thereto, and the bedding portion is positioned in adjacency to the at least one blade element 21 atop the support base 18 for compressibly receiving anterior portions of a blister pack cavity field 11 of a blister pack 10 (i.e. the blister pack 10 is inverted and received atop the bedding portion 20). The boundary portion 19 surrounds the bedding portion 20 and the least one blade element 21 for corralling a blister pack 10 as supported by the bedding field 20.

The at least one blade element 21 is configured for cutting through cavity-separating boundary portions 22 of the blister pack 10 when directed thereagainst under an externally applied force as at 120. The bedding portion is compressible during the externally applied force 120 and resiliently returnable when the externally applied force 120 is removed from the blister pack 10 thereafter being separated into individual blister pack units 16. The individual blister pack units 16 are then associated with (e.g. by inserting the units 16 into sleeves or packs 27) product-identifying barcode or machine readable code information as at 28, and thereby rendered scannable 110 via the scanner system 111 for inputting the product-identifying barcode or machine readable code information 28 to the non-transitory, computer-implementable application for processing.

A second phase of the system concerns a dispenser side of product management as opposed to the filler side of product management. In this regard, the computerized dispensary management system provides a basic dispenser screenshot as exemplified by initial basic dispenser screenshot 216. The basic dispenser screenshot comprises dispensing row sections as at row sections 226 for each listed product. The dispensing row sections 226 each terminate at a bifurcated upper and lower window arrangement or segment 220. Together the upper and lower windows 221 and 222 of the bifurcated segment(s) 220 provide at least a first dispensing column section as at 218 characterized by column-alternating upper and lower windows 221 and 222 overlapped with the listed row sections 226. The basic dispenser screenshot 216 may also preferably comprise the primary background coloration (e.g. blue coloration 60) that changes to a secondary, product-dispensed coloration (e.g. pink coloration 70) when a product item is correctly dispensed and an iterative number is added to a select window as selected from the upper and lower windows 221 and 222 of the bifurcated segment 220.

The blister pack separation apparatus 17 speeds blister pack separation into individual blister pack units 16 and preferably comprises a substantially rigid, incompressible support base; a blister pack-corralling boundary portion; a resilient, compressible cavity-field bedding portion; and at least one blade element. The blister pack-corralling boundary portion 19 is also preferably resiliently compressible or actuable as at 125 during the externally applied force 120 and resiliently returnable as at 126 when the externally provided or applied force 120 is removed therefrom.

The blister pack separation apparatus may preferably comprise a plurality of blade elements 21 whereby the bedding portion 20 extends intermediate at least two of the plurality of blades elements 21. The blister pack separation apparatus 17, when relaxed, may preferably further comprise a relaxed (bedding portion) height as at 143 and a relaxed (boundary portion) height as at 135. The relaxed boundary portion height 135 is greater than the relaxed bedding portion height 143 thereby providing a relaxed apparatus depth as at 131 in adjacency to the at least one, or plurality of blade element(s) 21.

The blister pack separation apparatus 17 cooperates with a blister pack 10 and a blister pack will necessarily comprise a blister pack depth or height as at 132. The blister pack depth or height is greater than the relaxed apparatus depth 131. Thus, the posterior portion 12 of the blister pack 10, when the anterior, cavity field portion 11 of the blister pack 10 is supported atop the bedding portion 20, is raised relative to the boundary portion 19. The blister pack separation apparatus may further preferably comprise a substantially rigid, incompressible cover element as at 24 for covering the blister pack 10 and interfacing between the at least one blade element 21 and the externally applied force for protecting an externally applied force source exemplified by drums 121 from damage via the at least one blade element 21

The cover element 24 may preferably be supported atop the blister pack 10 and engageable with the boundary portion 19 during compression or actuation of the blister pack separation apparatus 17. The boundary portion 19, extending peripherally about the bedding portion in a raised manner relative thereto and being compressible, stabilizes the cover element 24 during compression or actuation via the externally applied force.

Viewed methodologically, the present invention may be said to provide a computerized dispensary management method for enhancing dispensary product management comprising the steps of: providing a non-transitory, computer-implementable application for visually prompting a user via a visual display 39 in communication with at least one application-implementing computer 40; and prompting the user with a basic filler screenshot as at 61 upon the visual display 39 for filler side product management and inputting data to be processed by the non-transitory, computer-implementable application and the at least one application-implementing computer 40.

The method may be said to further comprise the step of scan-inputting as at 110 person-identifying barcode or machine readable code information as at 31 via a scanner system 111 in communication with the non-transitory, computer-implementable application and the at least one application-implementing computer 40; identifying a personal product regimen associated with the person-identifying barcode or machine readable code information 31; and displaying the personal product regimen upon the visual display 39 via the basic filler screenshot 61.

The basic filler screenshot 61 preferably comprises a maximum product regimen number as set forth in column section 103 and a scanned product entry number as set forth in column section 107. At least one product barcode or machine readable code 28 associated with the displayed personal product regimen is scan-input for adjusting the basic filler screenshot 61 with an iterative number in the column section 107. The personal product regimen may thus be filled when the maximum product regimen number matches the scanned product entry number as incrementally adjusted via the iterative number.

The computerized dispensary management method further contemplates the basic filler screenshot having a series of row sections and a series of column sections for visually tabulating information associated with the personal product regimen, such that the series of row sections enable a multiple product listing in a first column section, a second scanned product entry column, a third maximum product prescription column, and at least one time slot column. The step of removing a time-based information piece from the time slot column of a select row section when a successive new product barcode or machine readable code is scanned is contemplated.

The withdrawn information piece coincides with an iterative number, which iterative number is added to the scanned product entry column of the select row section. Recalling that a plurality of time slot columns may preferably extend in adjacency to one another, the information piece, when removed from the select time slot column, is preferably shifted to an adjacent time slot column. The information piece, when removed from the select time slot column, is shifted to an adjacent time slot column in the direction of the scanned product entry column.

Recalling that the basic filler screenshot preferably comprises a primary background coloration, the method may be said to further preferably comprise the step of changing the primary background coloration to a secondary, product-filled coloration in the select row section when the iterative number in the select row section matches a maximum product prescription number in the maximum product prescription column. Further, the method contemplates the steps of (s) displaying a visual alert in a message row section of the basic filler screenshot when a scanned product error is detected, and (b) changing the primary background coloration to a tertiary, product-error coloration in the message row section when the scanned product error is detected. An audible alert may also be provided when the scanned product error is detected for bolstering the visual alert.

The computerized dispensary management method may still further preferably comprise the step of providing a basic dispenser screenshot via the non-transitory, computer-implementable application. The basic dispenser screenshot operates for dispenser side product management, and comprises a series of dispensing row sections for listing each product as earlier filled. The dispensing row sections each terminate at a bifurcated upper-lower window segment. The bifurcated upper-lower window segments together provide at least a first dispenser column section characterized by column-alternating upper and lower windows overlapped with the dispensing row sections. The primary background coloration of the basic dispenser screenshot may preferably change to a secondary, product-dispensed coloration when a product item is correctly dispensed and an iterative number is added to a select window as selected from the bifurcated upper-lower window arrangement or segment.

The blister pack separation apparatus is believed to support certain preliminary steps of the dispensary management method, including the steps of: separating a blister pack into individual blister pack units via a blister pack separation apparatus substantially as earlier described and associating the separate individual blister pack units with product-identifying barcode or machine readable code information as at 28. The product-identifying barcode or machine readable code information 28 is scannable 110 via the scanner system 111 for inputting the product-identifying barcode or machine readable code information 28 to the non-transitory, computer-implementable application for processing.

Accordingly, although the invention has been described by reference to certain preferred and alternative systems, apparatus aspects, and methodologies, it is not intended that the novel arrangements be limited thereby, but that modifications thereof are intended to be included as falling within the broad scope and spirit of the foregoing disclosures, the appended drawings submitted in support of these specifications, and the following claims.

What is claimed is:

1. A computerized dispensary management system for enhancing dispensary product management, the computerized dispensary management system comprising:
   a non-transitory, computer-implementable application for implementing the dispensary management system according to dispensary system management rules and protocol;
   at least one application-implementing computer for implementing the non-transitory, computer-implementable application; and
   a scanner system for scan-inputting product-identifying and person-identifying code information to the non-transitory, computer-implementable application for processing, the person-identifying code information being scannable to identify a person and a product regimen for the person, the non-transitory, computer-implementable application for providing a series of sequential screenshots based upon a basic filler screenshot for filler side product management and guiding the user through a regimen-filling process, the regimen-filling process being characterized by screenshot re-arrangements visually and dynamically occurring to the basic filler screenshot each time a successive product code is scanned, the screenshot re-arrangements for enhancing dispensary product management:
   the basic filler screenshot comprising a series of row sections and a series of column sections for visually tabulating information concerning the product regimen, the series of row sections comprising a multiple product listing in a first column section, a scanned product entry column section, a maximum product prescription column section, and at least one time slot column section;
   an information piece in a select time slot column section being removed therefrom when a select successive product code is scanned, the information piece coinciding with an iterative number, the iterative number being added to the scanned product entry column section.

2. The computerized dispensary management system of claim 1 wherein a plurality of time slot column sections extend in adjacency to one another, the information piece, when removed from the select time slot column, being shifted to an adjacent time slot column section in the direction of the scanned product entry column section bearing a select iterative number.

3. The computerized dispensary management system of claim 1 wherein the basic filler screenshot comprises a primary background coloration, the primary background coloration changing to a secondary, product-filled coloration in a select row section when the iterative number in the select row section matches a maximum product prescription number in the maximum product prescription column section for the select row section.

4. The computerized dispensary management system of claim 1 wherein a basic dispenser screenshot is provided via the non-transitory, computer-implementable application for dispenser side product management, the basic dispenser screenshot comprising dispensing row sections for each listed product, the dispensing row sections each terminating at a bifurcated upper and lower window segment, together the upper and lower window segments providing at least a first dispensing column section characterized by column-alternating upper and lower windows overlapped with the listed row sections.

5. The computerized dispensary management system of claim 4 wherein the basic dispenser screenshot comprises a primary background coloration, the primary background coloration changing to a secondary, product-administered coloration when a select product item is correctly dispensed and an iterative number is added to a select window as selected from the bifurcated upper and lower window segment.

6. A computerized dispensary management method for enhancing dispensary product management, the computerized dispensary management method comprising the steps of:
- providing a non-transitory, computer-implementable application for visually prompting a user via a visual display in communication with at least one application-implementing computer;
- prompting the user with a basic filler screenshot upon the visual display for filler side product management and inputting data to be processed by the non-transitory, computer-implementable application and the at least one application-implementing computer;
- scan-inputting person-identifying code information via a scanner system in communication with the non-transitory, computer-implementable application and the at least one application-implementing computer;
- displaying a personal product regimen associated with the person-identifying code information upon the visual display via the basic filler screenshot, the basic filler screenshot (a) comprising a maximum product regimen number and a scanned product entry number and (b) providing a series of row sections and a series of column sections for visually tabulating information associated with the personal product regimen, the series of row sections providing a multiple product listing in an overlapping first column section, a second scanned product entry column section, a third maximum product prescription column section, and at least one time slot column section;
- scan-inputting at least one product code associated with the displayed personal product regimen, each scan-input product code adjusting the basic filler screenshot with an iterative number;
- filling the personal product regimen, the personal product regimen being filled when the maximum product regimen number matches the scanned product entry number as incrementally adjusted via the iterative number; and
- removing an information piece from the time slot column section of a select row section when a select successive product code is scanned, the information piece coinciding with the iterative number, the iterative number being added to the scanned product entry column section of the select row section.

7. The computerized dispensary management method of claim 6 wherein a plurality of time slot column sections extend in adjacency to one another, the information piece, when removed from the select time slot column section, being shifted to an adjacent time slot column section in the direction of the scanned product entry column section.

8. The computerized dispensary management method of claim 6 wherein the basic filler screenshot comprises a primary background coloration, the method comprising the step of changing the primary background coloration to a secondary, product-filled coloration in the select row section when the iterative number in the select row section matches a maximum product prescription number in the maximum product prescription column.

9. The computerized dispensary management method of claim 8 comprising the step of providing a basic dispenser screenshot via the non-transitory, computer-implementable application, the basic dispenser screenshot for dispenser side product management, the basic dispenser screenshot comprising dispensing row sections for each listed product, the dispensing row sections each terminating at a bifurcated upper and lower window segment, the bifurcated upper and lower window segments together providing at least a first dispenser column section characterized by column-alternating upper and lower windows overlapped with the dispensing row sections.

10. The computerized dispensary management method of claim 9 comprising the step of changing a primary background coloration of the basic dispenser screenshot to a secondary, product-administered coloration when a select product item is correctly administered and an iterative number is added to a select window as selected from the bifurcated upper and lower window segment.

* * * * *